United States Patent
Angermann et al.

(10) Patent No.: US 9,222,081 B2
(45) Date of Patent: Dec. 29, 2015

(54) METHOD OF PRODUCING AND PURIFYING AN ACTIVE SOLUBLE SIALYLTRANSFERASE

(75) Inventors: Axel Angermann, Dreieich (DE); Christian Scheckermann, Ehrenkirchen (DE); Karsten Schmidt, Karlsruhe (DE)

(73) Assignee: BIOGENERIX GMBH, Ulm (DE)

( * ) Notice: Subject to any disclaimer, the term of this patent is extended or adjusted under 35 U.S.C. 154(b) by 0 days.

(21) Appl. No.: 13/813,804

(22) PCT Filed: Aug. 2, 2011

(86) PCT No.: PCT/EP2011/063291
§ 371 (c)(1),
(2), (4) Date: Apr. 3, 2013

(87) PCT Pub. No.: WO2012/016984
PCT Pub. Date: Feb. 9, 2012

(65) Prior Publication Data
US 2014/0057316 A1    Feb. 27, 2014

(30) Foreign Application Priority Data
Aug. 2, 2010  (EP) .................................. 10171626

(51) Int. Cl.
C12P 21/06 (2006.01)
C12N 9/10 (2006.01)

(52) U.S. Cl.
CPC ....... *C12N 9/1081* (2013.01); *C12Y 204/99003* (2013.01)

(58) Field of Classification Search
None
See application file for complete search history.

(56) References Cited

U.S. PATENT DOCUMENTS

| 5,032,519 | A | 7/1991 | Paulson et al. |
| 6,280,989 | B1 | 8/2001 | Kapitonov et al. |
| 2006/0234345 | A1 | 10/2006 | Schwartz et al. |
| 2006/0246544 | A1 | 11/2006 | Kang et al. |
| 2008/0207487 | A1 | 8/2008 | DeFrees et al. |
| 2008/0253992 | A1* | 10/2008 | DeFrees et al. .............. 424/85.2 |

FOREIGN PATENT DOCUMENTS

| EP | 0737745 | 10/1996 |
| WO | WO 91/06635 | 5/1991 |
| WO | WO 2005/121332 | 12/2005 |
| WO | 2007056524 | 5/2007 |

OTHER PUBLICATIONS

Zhang et al., Biochemica et Biophysica Acta, 1998, vol. 1425 p. 441-452.*
Herrera et al., Biochemical and Biophysical Research Communication, 2000, vol. 273, p. 557-559.*
International Search Report and Written Opinion from corresponding PCT/EP2011/063291 application, mailed on Sep. 1, 2011, 11 pages.
Sticher U et al., "Purification and characterization of a (2-6)-sialytransferase from human liver", Glycoconjugate Journal, 8: 45-54 (1991).
Weinstein J et al., Journal of Biological Chemistry, 257 (22): 13835-13844, 1982.
Boyce FM and Buchner NL, Proc. Natl. Acad. Sci. USA, 93: 2348-2352, 1996.
Brondyk W.H., Methods in Enzymology, 463: 131-147, 2009 (abstract only) 2pgs.
Gillespie et al., J. Biol. Chem. 267(29): 21004-10, 1992.
Giovannini, Biotechnology and Bioengineering, 73: 522-529, 2001 (abstract only) 2pgs.
Gross et al., Anal Biochem, 186(1): 127-34, 1990 (abstract only) 2pgs.
Kitagawa and Paulson, J. Biol. Chem., 269: 1394-1401, 1994.
Kurosawa et al., J. Biol. Chem., 269: 1402-1409, 1994.
Lundstrom et al., Cytotechnology, 35: 213-221, 2001.
Nagata et al., Nature, 319: 415-418, 1986 (abstract only) 2pgs.
Nakayama J et al., Proc. Natl. Acad.Sci. USA, 92: 7031-7035, 1995.
Nakayama J et al., J. Biol. Chem., 271: 3684-3691, 1996.
Nara K et al., Proc. Natl.Acad. Sci. USA, 91: 7952-7956, 1994.
Paulson et al., J. Biol. Chem. 264: 17615-17618, 1989.
Shepard, J. of Chromatography, 891: 93-98, 2000 (abstract only) 2 pgs.
Skretas et al., Microbial Cell Factories, 8: 50, 2009.
Spiegel et al., J Chromatogr., 573(1): 23-7, 1992 (abstract only) 2pgs.
Tsuji S, J. Biochem, 120: 1-13, 1996.
Vola et al., Bio Techniques, 14: 650-655, 1993 (abstract only) 2pgs.

* cited by examiner

*Primary Examiner* — Kade Ariani
(74) *Attorney, Agent, or Firm* — Sheila R. Gibson; Hahn Loeser Parks LLP

(57) ABSTRACT

The present invention relates to a method for the production and purification of a sialyltransferase polypeptide, in particular a N-Acetylgalactosamine (Gal NAc)-α-2,6-sialyltransferase I (ST6GalNAcI) polypeptide. The method comprises the steps of producing the sialyltransferase polypeptide in a Chinese Hamster Ovary (CHO) cell and purifying the polypeptide with a combination of chromatography steps. The method results in high yield of sialyltransferase polypeptide which is highly pure and active. The obtained sialyltransferase, especially ST6GalNAcI, can be employed for the glycosylation of therapeutic proteins such as G-CSF.

20 Claims, 4 Drawing Sheets

METHOD OF PRODUCING AND PURIFYING AN ACTIVE SOLUBLE SIALYLTRANSFERASE

CROSS-REFERENCE TO RELATED APPLICATIONS

Figure 1:
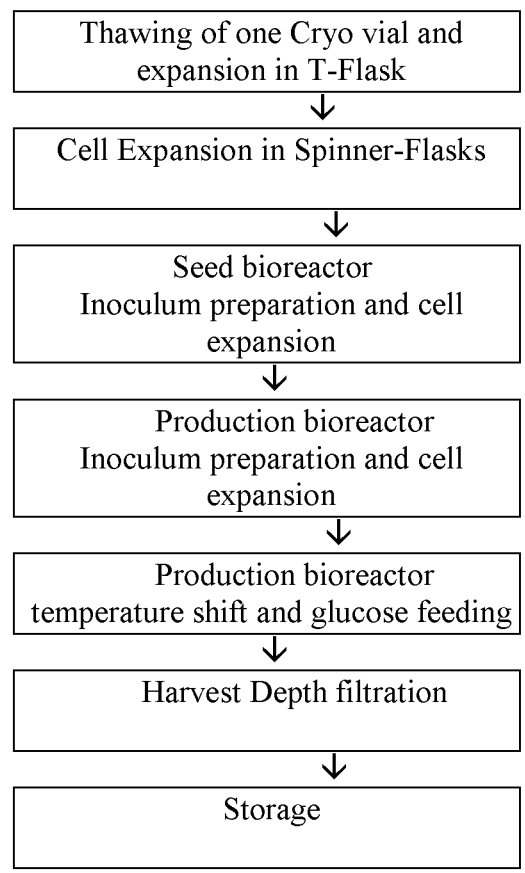

The present application is a U.S. National Stage entry under 35 U.S.C. §371 of International Application No. PCT/EP2011/063291, filed on 2 Aug. 2011, designating the United States of America and published in English on 9 Feb. 2012, which in turn claims priority to European Patent Application No. 10171626.4, filed on 2 Aug. 2010, each of which is hereby incorporated by reference in its entirety.

FIELD OF THE INVENTION

The present invention relates to a method for the production and purification of a sialyltransferase polypeptide, in particular a N-acetylgalactosamine (GalNAc)-alpha-2,6-sialyltransferase I (ST6GalNAcI) polypeptide. The method comprises the steps of producing the sialyltransferase polypeptide in Chinese Hamster Ovary (CHO) cells and purifying the polypeptide with a combination of chromatography steps. The method results in high yield of sialyltransferase polypeptide which is highly pure and enzymatically active. The obtained sialyltransferase, especially ST6GalNAcI, may be employed for the glycosylation of therapeutic proteins such as G-CSF.

BACKGROUND OF THE INVENTION

A great diversity of oligosaccharide structures and many types of glycopeptides are found in nature, and these are synthesized, in part, by a large number of glycosyltransferases. Glycosyltransferases catalyze the synthesis of glycolipids, glycopeptides and polysaccharides by transferring an activated mono- or oligosaccharide residue from a donor to an existing acceptor molecule to initiate or elongate a carbohydrate chain. A catalytic reaction is believed to involve the recognition of both the donor and acceptor by suitable domains of the glycosyltransferase, as well as the catalytic site of the enzyme.

More than 30% of all therapeutic proteins and many potential peptide therapeutics are glycosylated peptides. It is well known in the art that the attachment of the correct glycan structure can play a key role in the folding, biological activity, biodistribution and pharmacological efficacy of therapeutic peptides. Furthermore, glycosylation is a critically important factor influencing the in vivo half life and immunogenicity of therapeutic peptides. Indeed, humans will typically tolerate only those biotherapeutics that have particular types of carbohydrate attachments and will often reject glycoproteins that include non-mammalian oligosaccharide attachments. For instance, poorly glycosylated peptides are recognized by the liver as being "old" and thus, are more quickly eliminated from the body than are properly glycosylated peptides. In contrast, hyperglycosylated peptides or incorrectly glycosylated peptides can be immunogenic.

The production of a recombinant glycopeptide, in contrast to a recombinant non-glycosylated peptide, requires that a recombinantly produced peptide is subjected to additional processing steps, either in vivo within the cell or in vitro after the peptide has been produced by the cell. The peptide can be treated enzymatically, using a glycosyltransferase to introduce one or more glycosyl groups onto the peptide by covalently attaching the glycosyl group or groups to the peptide.

The production of a glycopeptide by external in vitro-steps of peptide processing can be time consuming and costly. This is due, in part, to the burden and cost of producing recombinant glycosyltransferases for the in vitro glycosylation of peptides and glycopeptides to produce glycopeptide therapeutics. As the demand and usage of recombinant glycotherapeutics increases, new methods are required in order to prepare glycopeptides more efficiently.

Moreover, as more and more glycopeptides are discovered to be useful for the treatment of a variety of diseases, there is a need for methods that lower the cost of their production. Further, there is also a need in the art to develop methods of more efficiently producing recombinant glycopeptides for use in developing and improving glycopeptide therapeutics.

Glycosyltransferases and their use for the glycosylation of proteins are disclosed in WO 2003/031464 A2.

Sialyltransferases constitute a family of glycosyltransferases that catalyze the posttranslational transfer of sialic acid (N-acetylneuraminic acid) to acceptor oligosaccharide substrates at terminal positions on glycoproteins and glycolipids (Paulson et al., 1989, *J. Biol. Chem.* 264: 17615-17618). It is estimated that the human genome encodes more than 20 different sialyltransferases required to synthesize all known sialo-oligosaccharide structures present in mammalian cells, but only 16 distinct human sialyltransferase cDNAs have been cloned (Tsuji S et al., 1996, *Glycobiology* 6: 5-7; Tsuji S, 1996, *J. Biochem.* 120:1-13; Weinstein J et al., 1982, *J. Biol. Chem.* 257: 13835-13844). Originally, sialyltransferases were biochemically purified and their cDNAs were cloned using N-terminal sequences. Comparison of the obtained cDNA sequences revealed two highly conserved regions, termed the L- and S-sialylmotifs, that participate in substrate binding. Subsequently, several sialyltransferases were cloned by PCR using degenerate primers designed within the sialylmotifs or by expression cloning (Nara K et al., 1994, *Proc. Natl. Acad. Sci. USA* 91: 7952-7956; Nakayama J et al., 1996, *J. Biol. Chem.* 271: 3684-3691; Nakayama J et al., 1995, *Proc. Natl. Acad. Sci. USA* 92: 7031-7035). Gene cloning by differential display adds an entirely different approach to the identification of novel sialyltransferases with putative functional significance in disease-related processes.

Sialyltransferases differ in their substrate specificity and tissue distribution, and they are classified into four families according to the carbohydrate linkages they synthesize: the ST3Gal-, ST6Gal-, ST6GalNAc-, and ST8Sia-families. The members of each family exhibit strong activity towards certain acceptor groups, although the substrate specificities of these enzymes overlap; one linkage can be synthesized by multiple enzymes.

One such particular sialyltransferase that has utility in the development and production of therapeutic glycopeptides is N-acetylgalactosamine-α2,6-sialyltransferase (ST6GalNAcI) which catalyzes the transfer of sialic acid from a sialic acid donor to a sialic acid acceptor. Full length chicken ST6GalNAcI enzyme, for example, is disclosed by Kurosawa et al. (1994, *J. Biol. Chem.*, 269:1402-1409).

In the past, there have been efforts to increase the availability of recombinant sialyltransferases for the in vitro production of glycopeptides.

EP 0 737 745 A1 and U.S. Pat. No. 5,032,519 of the Institute of Physical & Chemical Research refer to the use of *E. coli* for producing a secreted version of a protein comprising a portion, i.e. active domain, that is derived from ST6GalNAcI and is responsible for its activity.

WO 2007/056524 A2 of Neose Technologies Inc. describes methods of producing a modified ST6GalNAcI polypeptide, the method comprising growing a recombinant prokaryotic host cell under conditions suitable for expression of the modified ST6GalNAcI polypeptide in prokaryotic host cells. These modified ST6GalNAcI polypeptides are chimeric polypeptides comprising a first portion from a Gal-β1,3GalNAc-α2,3-sialyltransferase (ST3GalI) polypeptide and a second portion from a GalNAc-α-2,6-sialyltransferase I (ST6GalNAcI) polypeptide. Modified ST6GalNAcI polypeptides can further be truncated polypeptides lacking all or portion of the ST6GalNAcI signal domain, all or a portion of the ST6GalNAcI transmembrane domain, and/or all or a portion of the ST6GalNAcI stem domain in eukaryotic or prokaryotic host cells.

US 2006/0234345 A1 of Neose Technologies Inc. discloses a method of producing a soluble eukaryotic glycosyltransferase in a prokaryotic microorganism that has an oxidizing environment, by a) expressing a nucleic acid that encodes the eukaryotic glycosyltransferase in the prokaryotic microorganism; and then b) growing the prokaryotic microorganism under conditions that allow expression of the soluble active eukaryotic glycosyltransferase within a cellular compartment of the prokaryotic microorganism.

Skretas et al. (2009, *Microbial Cell Factories*, 8:50) relate to a method for the expression of the human sialyltransferase ST6GalNAcI in engineered *E. coli* strains which possess certain types of oxidative cytoplasm or which co-express the molecular chaperones/co-chaperones trigger factor, DnaK/DnaJ, GroEL/GroES, and Skp, and can produce greatly enhanced amounts of soluble ST6GalNAcI.

However, the capacity of *E. coli* for protein folding and forming disulfide bonds is not sufficient although there are a number of tools developed to overcome these limitations. Furthermore, the high expression yield of recombinant proteins in *E. coli* expression systems can often lead to the accumulation of aggregated, insoluble proteins that form inclusion bodies which can be a significant hindrance in obtaining soluble, active proteins (Brondyk W. H., 2009, *Methods in Enzymology*, Vol. 463, Ch. 11).

To overcome the problems associated with recombinant sialyltransferase production in *E. coli* cultures, insect cell culture systems have been developed.

US 2006/0246544 A1 and US 2008/0207487 A1 disclose a method of making a composition that includes a recombinant polypeptide, e.g. sialyltransferases, wherein the polypeptide is expressed in an insect cell (e.g., using a baculoviral expression system) and wherein the composition is essentially free of endoglycanase activity. The method includes subjecting a mixture including the polypeptide to mixed-mode chromatography including the steps of: (i) contacting the mixture and a mixed-mode chromatography medium; and (ii) eluting the polypeptide from the mixed-mode chromatography medium generating a flow-through fraction comprising the polypeptide.

However, the complexity of the baculovirus-insect cell expression system, the limited storage stability of the required viral seed stocks and the requirement of very high virus titers for an efficient infection can limit its use for large-scale bioproduction. Furthermore, viral vectors such as baculovirus have been shown to be able to infect mammalian cells, particularly human cells (Boyce F M and Buchner N L, 1996, *Proc. Natl. Acad. Sci. USA* 93:2348-2352; Lundstrom et al., 2001, *Cytotechnology*, 35: 213-221). Thus, these vectors pose a threat concerning safety issues, especially when applied for large-scale recombinant protein production, where large volumes of infected cells are handled.

An alternative to overcome the described limitations of the use of insect cell culture systems is the use of mammalian cell systems for the manufacture of recombinant sialyltransferases.

WO 2005/121332 A2 of Neose Technologies Inc. discloses methods of producing isolated truncated ST6GalNAcI polypeptide that lacks all or a portion of the ST6GalNAcI signal domain, all or a portion of the ST6GalNAcI transmembrane domain, and/or all or a portion of the ST6GalNAcI stem domain in prokaryotic and insect host cells and generally mentions that the polypeptide may also be produced in mammalian cells.

U.S. Pat. No. 5,032,519 of the University of California describes methods of transfecting a host cell, e.g. a CHO cell, with a vector carrying a gene which expresses a glycosyltransferase that has the membrane anchor and most of the stem region replaced with a cleavable secretion signal segment. The resulting soluble glycosyltransferase, when expressed in the cell, is secreted by the cell. The secreted soluble glycosyltransferase is then separated from the cell culture media for use in industrial applications or carbohydrate synthesis research. Further, U.S. Pat. No. 5,032,519 discloses a method of purifying a soluble glycosyltransferase by using an affinity chromatography.

However, none of the mentioned documents relating to the production of recombinant sialyltransferases in mammalian cells discloses a method for providing a recombinant sialyltransferase which is highly active, purified to a pharmaceutical grade and amenable to large scale production.

Therefore, a need still exists for efficient methods of production of recombinant sialyltransferases having activity and purity that are suitable for "pharmaceutical-scale" processes and reactions, especially for the production of glycopeptide therapeutics. Thus, the problem underlying the present invention is to provide such methods for producing recombinant sialyltransferases.

SUMMARY OF THE INVENTION

This problem is solved according to the present invention by providing, in one aspect, a method of producing a sialyltransferase polypeptide, which comprises the steps of:
a) expressing a sialyltransferase polypeptide in a CHO cell; collecting the culture medium containing the expressed sialyltransferase polypeptide; and
b) purifying the sialyltransferase polypeptide from the culture medium by subjecting the cell culture medium to (i) at least one affinity chromatography and/or one mixed-mode chromatography step and (ii) at least one anion exchange chromatography and/or one cation exchange chromatography step.

In one embodiment, the sialyltransferase polypeptide is a truncated sialyltransferase polypeptide lacking all or portion of the sialyltransferase signal domain, all or portion of the sialyltransferase transmembrane domain, and/or all or portion of the sialyltransferase stem domain. Preferably, the sialyltransferase polypeptide only comprises the sialyltransferase active domain.

In a preferred embodiment, the sialyltransferase is ST6GalNAcI. Typically, the ST6GalNAcI is selected from the group consisting of: human, chimpanzee, orangutan, pig, cow, dog, rat, mouse and chicken ST6GalNAcI. In a preferred embodiment, the ST6GalNAcI is a chicken ST6GalNAcI. Most preferably, the ST6GalNAcI polypeptide comprises an amino acid sequence according to SEQ ID NO:4 or SEQ ID NO: 6. According to an embodiment of the present invention, an expression cassette encoding an EPO signal sequence and a sialyltransferase polypeptide sequence is used for expressing the sialyltransferase polypeptide in CHO cells.

Preferably, step a) of the production method is performed by using a serum-free fed-batch culture and/or by performing an incubation temperature shift from 37° C.+/−1° C. to 32° C.+/−1° C. after reaching a predefined cell density.

Further, the invention includes methods wherein step c) comprises two affinity chromatography processes or one affinity chromatography process and one mixed-mode chromatography process, one anion exchange chromatography process and one cation exchange chromatography process. In a most preferred embodiment, step c) is performed in the following order:
  i. an anion exchange chromatography;
  ii. a first affinity chromatography;
  iii. a second affinity chromatography or a mixed-mode chromatography;
  iv. a cation exchange chromatography.

Typically, the anion exchange chromatography is performed with anion exchange resins or membranes that contain Diethylaminoethyl-groups (DEAE), quaternary aminoethyl-groups (QAE), quaternary ammonium-groups (Q), Dimethylaminoethyl-groups (DMAE) and/or Trimethylaminoethyl-groups (TMAE) as functional groups. Preferably it is performed with a commercially available Q-Sepharose Fast Flow resin, using a NaCl/Tris-HCl buffer as eluent at a pH in the range between 7.0 and 8.0.

Generally, the affinity chromatography is performed with Ni-NTA resins, Talon resins, dye chromatography resins, antibody-affinity resins, lectin affinity resins and/or peptide-ligand-affinity resins. In a preferred embodiment, the (first) affinity chromatography is performed with a commercially available Blue Sepharose FF resin, preferably using a L-arginine hydrochloride/potassium phosphate buffer at a pH in the range between 7.0 and 8.0 as eluent and the mixed-mode chromatography is performed with a commercially available hydroxyapatite resin, preferably using a NaCl/potassium phosphate buffer at a pH in the range between 7.0 and 8.0 as eluent.

Typically, the cation exchange chromatography is performed with a resin that contains sulfopropyl cation exchange material or a resin having similar characteristics. Preferably it is performed with a commercially available SP-Sepharose High Performance resin, more preferably using a NaCl/potassium phosphate buffer at a pH in the range between 6.0 and 7.0 as eluent.

In another aspect, the present invention provides a sialyltransferase polypeptide produced by any one of the methods according to the invention, wherein the sialyltransferase polypeptide is at least 98% pure, preferably at least 99% pure, most preferably more than 99% pure. In a preferred embodiment, the sialyltransferase polypeptide is ST6GalNAcI.

In a further aspect, the present invention includes the use of the ST6GalNacI polypeptide produced by any one of the methods according to the invention for the glycosylation of therapeutic proteins, such as for the glycosylation of human cytokines, in particular for the glycosylation of human granulocyte-colony stimulating factor, G-CSF.

DETAILED DESCRIPTION OF THE INVENTION

The present invention provides a method for the production and purification of an improved sialyltransferase which is highly active and pure. This objective is achieved by expressing a sialyltransferase polypeptide in a CHO cell, collecting the cell culture medium containing the expressed sialyltransferase polypeptide, and purifying the sialyltransferase polypeptide from the culture medium by subjecting the culture medium to (i) at least one affinity chromatography and/or one mixed-mode chromatography process and (ii) at least one anion exchange chromatography and/or one cation exchange chromatography process.

More specifically, the present invention relates to a method where the purification of the sialyltransferase polypeptide is performed in the following order:
  i. an anion exchange chromatography;
  ii. a first affinity chromatography;
  iii. a second affinity chromatography or a mixed-mode chromatography;
  iv. a cation exchange chromatography.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein.

A. Sialyltransferase Polypeptide and Expression Cassette

In one embodiment, the sialyltransferase polypeptide is a truncated sialyltransferase polypeptide lacking all or portion of the sialyltransferase signal domain, all or portion of the sialyltransferase transmembrane domain, and/or all or portion of the sialyltransferase stem domain. Preferably, the sialyltransferase polypeptide only comprises the sialyltransferase active domain. The sialyltransferase polypeptide can further comprise a signal peptide.

In a preferred embodiment, an expression cassette encoding an EPO signal sequence and a sialyltransferase polypeptide sequence is used for expressing a sialyltransferase polypeptide in CHO cells.

"Polypeptide", alternatively referred to as a "protein", refers to a polymer in which the monomers are amino acids and are joined together through amide bonds. Additionally, unnatural amino acids, for example, P-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see Spatola, A. F., in "Chemistry and biochemistry of amino acids, peptides and proteins", B. Weinstein, eds., Marcel Dekker, New York, p. 267 (1983). The term polypeptide includes molecules that are commonly referred to as proteins or peptides.

The sialyltransferase polypeptide can be any sialyltransferase polypeptide known to those of ordinary skill in the art, comprising but not being limited to: α-(2,3)sialyltransferase (ST3Gal3) (Kitagawa and Paulson, 1994, *J. Biol. Chem.* 269: 1394-1401), α-N-acetylgalactosamide α-2,6-sialyltransferase I (ST6GalNAcI) (Kurosawa et al., 1994, *J. Biol. Chem.*, 269: 1402-1409), and β1,3GalNAc-α2,3-sialyltransferase (ST3GalI) (Gillespie et al., 1992, *J. Biol. Chem.* 267(29): 21004-10).

A "truncated sialyltransferase polypeptide" refers to a sialyltransferase that has fewer amino acid residues than a naturally occurring sialyltransferase, but that retains enzymatic activity. Any number of amino acid residues can be deleted as long as the enzyme retains activity. In some embodiments, domains or portions of domains can be deleted. In a preferred embodiment of the present invention, the sialyltransferase polypeptide only comprises the sialyltransferase active domain.

An "active domain" or "catalytic domain" refers to a protein domain, or a subsequence thereof, that catalyzes an enzymatic reaction performed by the enzyme. For example, a catalytic domain of a sialyltransferase will include a subsequence of the sialyltransferase sufficient to transfer a sialic acid residue from a donor to an acceptor saccharide. A catalytic domain can include an entire enzyme, a subsequence thereof, or can include additional amino acid sequences that are not attached to the naturally occurring enzyme, or a subsequence thereof. An exemplary catalytic region is, but is not limited to, the catalytic domain of chicken ST6GalNacI, which comprises amino acid residues from 232 to 566 of the full-length sequence according to SEQ ID NO: 2. The catalytic domain of chicken ST6GalNacI is depicted in SEQ ID No. 4. In a preferred embodiment, the sialyltransferase is ST6GalNAcI. Typically, the ST6GalNAcI is selected from the group consisting of: human, chimpanzee, orangutan, pig, cow, dog, rat, mouse and chicken ST6GalNAcI (Kurosawa et al., 1994, *J. Biol. Chem.*, 269:1402-1409; Skretas et al., 2009, *Microbial cell factories*, 8:50; WO 2005/121332). In a most preferred embodiment, the ST6GalNAcI is a chicken ST6GalNAcI which is encoded by the nucleotide sequence of SEQ ID NO: 1. Preferably, the ST6GalNAcI polypeptide is encoded by the nucleotide sequence according to SEQ ID NO: 3 or SEQ ID NO: 5 and has an amino acid sequence according to SEQ ID NO: 4 or SEQ ID NO: 6, respectively.

B. Expression System

According to the present invention, the sialyltransferase polypeptide is expressed in a CHO cell or an equivalent cell line known by one of ordinary skill in the art. The particular procedure used to introduce the respective genetic material into the host cell for expression of the soluble sialyltransferase is not particularly critical. As will be understood by the skilled artisan, the choice of promoter, as well as methods and strategies for introducing genetic material into the host cell used for expressing a sialyltransferase polypeptide of the invention are well-known in the art.

These include the use of plasmid vectors, viral vectors and any of the other well known methods for introducing cloned genomic DNA, cDNA, synthetic DNA or other foreign genetic material into a host cell. It is only necessary that the particular genetic engineering procedure utilized be capable of successfully introducing at least one gene into the host cell which is capable of expressing the full-length or genetically modified or truncated sialyltransferase.

A "vector" is a composition of matter which comprises an isolated nucleic acid and which can be used to deliver the isolated nucleic acid to the interior of a cell. Various kinds of vectors are known in the art including, but not limited to, linear nucleic acids, nucleic acids associated with ionic or amphiphilic compounds, plasmids, and viruses. Thus, the term "vector" includes an autonomously replicating plasmid or a genetically modified virus. The term should also be construed to include non-plasmid and non-viral compounds which facilitate transfer of nucleic acid into cells, such as, for example, polylysine compounds, liposomes, and the like.

Suitable vectors include pSV40, pEF-1-α, pSV2, pT-Rex, pSecTag2, pBudCE4.1, or pcDNA/His Max vector, along with, for example, a CMV promoter. In a preferred embodiment of the present invention, the pMOZ-G8 vector which is designed for high level expression of a heterologous gene is used for the expression of the sialyltransferase polypeptide. Suitable selection markers are, among others, neomycin, puromycin, hygromycin and dihydrofolate reductase (DHFR).

C. CHO Cell Culture

According to an embodiment of the present invention, step a) of the production method is performed by using a serum-free fed-batch culture and by using an incubation temperature shift from 37° C.+/−1° C. to 32° C.+/−1° C. after reaching a predefined cell density of ≥$5×10^5$ viable cells/mL, preferably ≥$1.5×10^6$ viable cells/mL. The present inventors have found that this temperature shift increases the viability of the cells so that they can be kept in culture for a longer period. This in turn results in a higher product yield.

For example, without temperature shift the cells can only be cultured for five days and a product yield of about 24 mg/l is obtained. In contrast, if a temperature shift is applied, the cells can be cultured for nine days and a product yield of 68 mg/l is obtained.

The sialyltransferase polypeptide is produced in serum-free fed-batch culture using a CHO derived cell line engineered to overexpress ST6GalNAcI. The inoculum for the fermentation process is grown from one vial of the master cell bank (MCB) using T-flasks or spinner flasks followed by cultivation in a seed bioreactor. The inoculum is then transferred to the production bioreactor where further cell expansion occurs until the cell density has reached an appropriate level for production.

A temperature shift is initiated at a defined cell density and the glucose level is maintained within a defined range by feeding of a glucose solution. At the end of the cultivation the culture is harvested. Cells and debris in the culture are removed from the harvest by depth filtration. The harvest is stored at 2-8° C. until the start of the protein purification.

FIG. 1 illustrates the different cell culture and harvest steps of a preferred embodiment of the present invention.

D. Purification of Sialyltransferase

According to a further aspect of the present invention, the purification of the sialyltransferase polypeptide from the culture medium is performed by subjecting the culture medium to at least one affinity chromatography step and/or mixed mode chromatography step and at least one anion and/or cation exchange chromatography step.

In a preferred embodiment, the purification is achieved in the following order:
  i. an anion exchange chromatography, which concentrates enzyme containing solution and provides a first reduction of contaminants such as DNA, host cell proteins (HCP) and fermentation medium compounds;
  ii. a first affinity chromatography, which is used as intermediate purification step to enrich the sialyltransferase enzyme and deplete host cell proteins;
  iii. a second affinity chromatography or a mixed-mode chromatography, which is used to effectively reduce host cell protein level; and
  iv. a cation exchange chromatography, which is used to remove any residual host cell protein and other contaminants.

Figure 2:
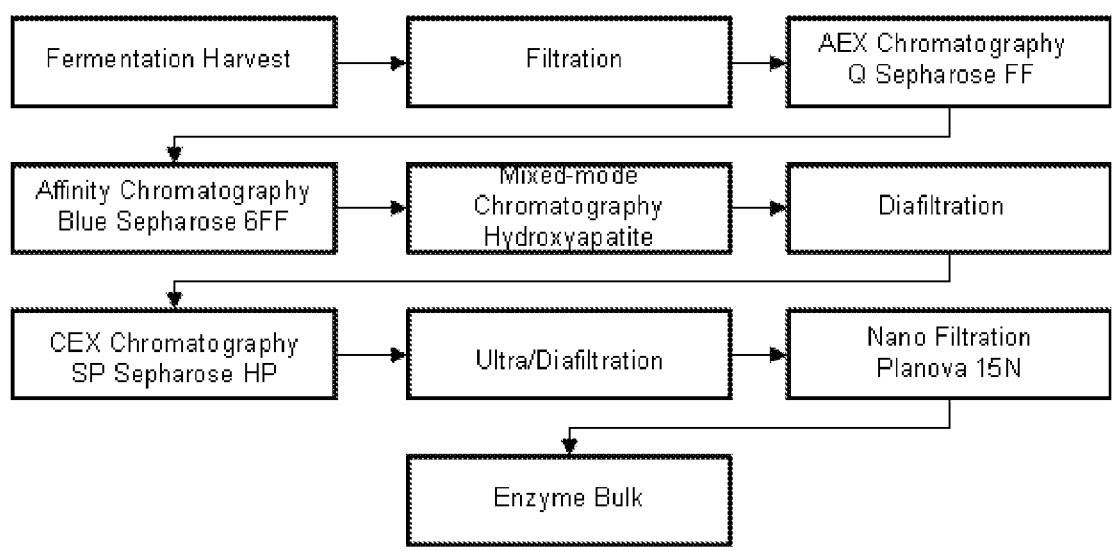

FIG. 2 illustrates the different purification steps of a preferred embodiment of the present invention.

I. Anion Exchange Chromatography Step

According to an embodiment of the present invention, the sialyltransferase polypeptide purification process includes an anion exchange chromatography (AEC) step.

AEC relies on charge-charge interactions between the proteins in the sample and the charges immobilized on the resin.

In anion exchange chromatography, the binding ions of the proteins are negative, and the functional group immobilized on the resin is positive. Commonly used anion exchange resins are Q-resin, a quaternary amine, and DEAF resin (Di-EthylAminoEthane). However, in general the anion exchange chromatography step can be performed with all common commercially available anion exchange resins or membranes. Anion exchange resins may be used in the form of pre-packed columns. Alternatively, columns may be self-prepared. There are no specific limitations as to the capacity and the geometry of the columns other than the usual ones. The person skilled in the art knows that the amount of anion exchange resin to be used depends on the overall protein content of the cell culture fluid or any other fluid, e.g., the eluate of a preceding chromatography step, applied to the column in the capture step.

Typical strong anion exchange resins that can be used for the purpose of the invention comprise functional groups such as: quaternary aminoethyl (QAE) moieties, quaternary ammonium (Q) moieties and trimethylammoniumethyl (TMAE) groups.

Resins having quaternary aminoethyl (QAE) moieties include, e.g., Toyopearl QAE (available from Tosoh Bioscience, Germany), Selectacel QAE (a quaternary aminoethyl derivative of cellulose, available from Polysciences Inc., Pennsylvania USA) and others. Resins having quaternary ammonium (Q) moieties include, e.g., Q Sepharose XL, Q Sepharose FF, Q Sepharose HP, Resource Q (available from GE Healthcare, Germany), Macro Prep High Q (Bio-Rad, California, USA), Toyopearl Super Q (available from Tosoh Bioscience, Germany) and UNOsphere Q (available from Bio-Rad, California, USA). Resins having trimethylammoniumethyl (TMAE) groups include, e.g., Fractogel EMD TMAE (available from Merck, Germany).

The anion exchange chromatography is preferably a strong anion exchange chromatography which is performed using a strong anion exchange resin having—$N^+(CH_3)_3$ functional groups, or a resin having similar characteristics. Preferred examples of strong anion exchange resins which can be used for the purpose of the invention are quaternary ammonium strong anion exchanger resins known in the art as UNOsphere Q, Q Sepharose HP, Q Sepharose FF and other resins having quaternary ammonium (Q) moieties. In a most preferred embodiment of the present invention, the anion exchange chromatography is performed with a commercially available Q-Sepharose Fast Flow resin.

The step of anion exchange chromatography is preferably carried out using equilibration buffers having a mildly alkaline pH. Suitable buffers include, for example, borate buffer, triethanolamine/iminodiacetic acid, Tris, ammonium acetate, tricine, bicine, TES, HEPES, TAPS. The use of a Tris buffer is preferred, more preferably the buffer contains 20 mM Tris at a pH of 7.6. The anion exchange resin is washed one or more times with the equilibration buffer and the flow-through fraction is discarded. Elution from the anion exchange resin is usually achieved by increasing the conductivity of the mobile phase through the addition of salt, preferably sodium chloride. Preferably, the anion exchange chromatography is performed using a NaCl/Tris-HCl buffer as eluent at a pH in the range between 7.0 and 8.0. More preferably, the elution buffer contains 800 mM NaCl and 20 mM Tris/HCl at a pH of 7.6.

II. First Affinity Chromatography Step

According to an embodiment of the present invention, the sialyltransferase polypeptide purification process includes an affinity chromatography step which preferably is a dye affinity chromatography.

In a preferred embodiment the method of purifying the sialyltransferase polypeptide comprises a single affinity chromatography step, more preferably the single affinity chromatography step is a dye affinity chromatography step.

Dye affinity chromatography is based on the high affinity of immobilized dyes for binding sites on the proteins of the sample. The step of dye affinity chromatography is carried out using a resin having as an immobilised ligand a dye compound which is well known to a person skilled in the art, i.e., Cibacron Blue F3G-A. The term "immobilized" is well understood by a person skilled in the art and means that the ligand is derivatised in the sense that it is chemically linked to the resin. A particularly preferred resin is Blue Sepharose FF (obtainable from Amersham Biosciences Inc.).

It is understood that the method may be performed with alternative resins, having similar characteristics. Examples of alternative resins include: Toyopearl AF-blue-HC-650M (Tosoh Bioscience), Toyopearl SuperButyl 550, Toyopearl Phenyl 650, Blue Cellthru BigBead (Sterogene), SwellGel Blue (Pierce), Cibachrome blue 3GA-agarose 100 (Sigma), Affi-Gel Blue (BioRad), Econo-Pac blue cartridges (Bio-Rad), Blue sepharose HP (Amersham), Cibacron Blue 3GA (Sigma), Blue Sepharose 6FF (GE Healthcare), ProSep PB (Millipore), Methyl Sepharose and CDP Sepharose (Calbiochem).

The step of dye affinity chromatography is preferably carried out using equilibration buffers having a mildly alkaline pH. Suitable buffers include, for example, MES, Bis-Tris, ADA, PIPES, ACES, BES, MOPS, TES, HEPES. Preferably, the equilibration buffer comprises potassium phosphate buffer and NaCl. More preferably, the equilibration buffer comprises 25 mM potassium phosphate buffer, pH 7.5 and 50 mM NaCl. The affinity resin is washed one or more times with the equilibration buffer and the flow-through fraction is discarded. In a more preferred embodiment, the dye affinity chromatography is performed using an L-arginine hydrochloride/potassium phosphate buffer at a pH in the range between 7.0 and 8.0 as eluent. Most preferably, the protein is eluted with a buffer containing 500 mM L-arginine hydrochloride and 25 mM potassium phosphate at a pH of 7.5.

III. Second Affinity Chromatography Step or Mixed-Mode Chromatography

According to an embodiment of the present invention, the sialyltransferase polypeptide purification process includes a second affinity chromatography step as described in previous chapter II or a mixed-mode chromatography, preferably a hydroxyapatite chromatography.

Hydroxyapatite chromatography is a mixed mode chromatography that utilizes an insoluble hydroxylated calcium phosphate $Ca_{10}(PO_4)_6(OH)_2$, which forms both the matrix and ligand. Functional groups consist of pairs of positively charged calcium ions (C-sites) and clusters of negatively charged phosphate groups (P-sites). The interactions between hydroxyapatite and proteins are complex and multi-mode. In one method of interaction, positively charged amino groups on proteins associate with the negatively charged P-sites and negatively charged carboxyl groups on the protein interact by coordination complexation to C-sites (Shepard (2000) *J. of Chromatography* 891:93-98).

Crystalline hydroxyapatite was the first type of hydroxyapatite used in chromatography. Ceramic hydroxyapatite chromatography is a further development in hydroxyapatite chromatography. Ceramic hydroxyapatite refers to a form of hydroxyapatite in which nanocrystals are agglomerated into particles and fused at high temperature to create stable ceramic microspheres suitable for chromatography applications. Commercial examples of ceramic hydroxyapatite include, but are not limited to, CHT Type I and CHT Type II.

Ceramic hydroxyapatite has high durability, good protein binding capacity, and can be used at higher flow rates and pressures than crystalline hydroxyapatite. (Vola et al. (1993) *BioTechniques* 14:650-655). Hydroxyapatite has been used in the chromatographic separation of proteins, nucleic acids, as well as antibodies. In hydroxyapatite chromatography, the column is usually equilibrated, and the sample applied, in a low concentration of phosphate buffer and the adsorbed proteins are then eluted in a concentration gradient of phosphate buffer (Giovannini, (2000) *Biotechnology and Bioengineering* 73:522-529).

Any hydroxyapatite resin may be used to carry out the mixed mode chromatography step of the method according to the invention. In a preferred embodiment, it is carried out on a ceramic hydroxyapatite resin, such as a type I or type II hydroxyapatite resin. The hydroxyapatite resin may have particles of any size such as 20, 40 or 80 µm. In a highly preferred embodiment, the ceramic hydroxyapatite resin comprises particles having a size of 40 µm. A hydroxyapatite resin that is particularly suitable is a column commercially available under the name CHT Ceramic hydroxyapatite Type I, 40 µm.

The equilibration buffer preferably comprises a potassium phosphate buffer at a pH between 6.3 and 7.3, more preferably it comprises 5 mM potassium phosphate buffer, pH 6.8. The hydroxyapatite resin is washed one or more times with the equilibration buffer and the flow-through fraction is discarded. In a more preferred embodiment of the present invention, the hydroxyapatite affinity chromatography is performed using a NaCl/potassium phosphate buffer at a pH in the range between 6.3 and 7.3 as eluent. Most preferably, the elution buffer contains 5 mM potassium phosphate buffer and 1 M NaCl at a pH of 6.8.

IV. Cation Exchange Chromatography Step

According to an embodiment of the present invention, the sialyltransferase polypeptide purification process includes a cation exchange chromatography (CEC) step.

CEC relies on charge-charge interactions between the proteins in the sample and the charges immobilized on the resin. In cation exchange chromatography, the binding ions of the proteins are positive and the immobilized functional group is negative. Commonly used cation exchange resins are S-resin, sulfate derivates, and CM (carboxymethyl) resins, carboxylated derived ions.

However, in general the cation exchange chromatography step can be performed with all common commercially available cation exchange resins or membranes. Cation exchange resins may be used in the form of pre-poured columns or membranes on which the functional group, e.g., sulfonic acid, is fixed. Alternatively columns may be self-prepared. There are no specific limitations as to the capacity and the geometry of the columns other than the usual ones. The person skilled in the art knows that the amount of cation exchange resin to be used depends on the overall protein content of the cell culture fluid or any other fluid, e.g., the eluate of a preceding chromatography step.

Different types of cation exchange materials are available under different names and from a multitude of suppliers such as Bio-Rex® (e.g., type 70), Chelex® (e.g., type 100), Macro-Prep® (e.g., type CM, High S, 25 S), AG® (e.g., type 50W, MP) (all available from BioRad Laboratories); WCX 2 (available from Ciphergen), Dowex® MAC-3 (available from Dow Chemical company), Mustang C and Mustang S (available from Pall Corporation), Cellulose CM (e.g., type 23, 52), hyper-D, partisphere (available from Whatman plc.), Amberlite® IRC (e.g., type 76, 747, 748), Amberlite® GT 73, Toyopearl® (e.g., type SP, CM, 650M) (all available from Tosoh Bioscience GmbH), CM 1500 and CM 3000 (available from BioChrom Labs), SP-Sepharose™, CM-Sepharose™ (available from GE Healthcare), Porous resins (available from PerSeptive Biosystems), Asahipak ES (e.g., type 502C), CXpak P, IEC CM (e.g., type 825, 2825, 5025, LG), IEC SP (e.g., type 420N, 825), IEC QA (e.g., type LG, 825) (available from Shoko America Inc.), 50W cation exchange resin (available from Eichrom Technologies Inc.). Preferably the cation exchange material is a strong cation exchange material such as Macro-Prep® High 5 or 25S, MacroCap SP, Toyopearl® SP 650M, Source S, SP Sepharose, or POLYCAT A.

In a preferred embodiment of the present invention, the cation exchange step is performed with a resin that contains sulfopropyl cation exchange material or a resin having similar characteristics. In a most preferred embodiment of the present invention, the cation exchange chromatography is performed with a commercially available SP-Sepharose High Performance resin.

The step of cation exchange chromatography is preferably carried out using an equilibration buffer having a mildly acidic pH. Suitable buffers include, for example, maleic acid, malonic acid, citric acid, lactic acid, formic acid, butaneandioic acid, acetic acid, phosphate, HEPES and BICINE. The use of a phosphate buffer is preferred, more preferably the equilibration buffer contains 25 mM potassium phosphate buffer at a pH of 6.0. The cation exchange resin is washed one or more times with the equilibration buffer and the flow-through fraction is discarded. Elution from the cation exchange resin is usually achieved by increasing the conductivity of the mobile phase through the addition of salt, preferably sodium chloride. Preferably, the cation exchange chromatography is performed using a NaCl/potassium phosphate buffer at a pH in the range between 6.0 and 7.0 as eluent. More preferably, the elution buffer contains 250 mM NaCl and 25 mM potassium phosphate having a pH of 6.0.

V. Further Purification Steps

Furthermore, the method can comprise filtration steps. Filtration processes are well known by the person skilled in the art and all common methods can be used. The method can comprise one or more ultrafiltration processes at diverse steps of the method. The method can comprise nanofiltration, e.g., for final virus clearance.

Ultrafiltration is a form of membrane filtration in which hydrostatic pressure forces a liquid against a semipermeable membrane. Suspended solids and solutes of high molecular weight are retained, while water and low molecular weight solutes pass through the membrane. Ultrafiltration is a commonly used method of separation for purifying and concentrating macromolecular solutions, especially protein solutions. Ultrafiltration is similar to nanofiltration, however, differing in terms of the size of the molecules it retains. In the framework of the present invention, a molecular weight cut off of 10 kDa is preferred (10 kDa UF). UF membranes may also be used for diafiltration to remove salts and other microspecies from solution via repeated or continuous dilution and reconcentration.

Preferably, the process of purification comprises one or more ultrafiltration/diafiltration steps. These filtration steps can be performed before, between and/or after the chromatography steps. Preferably, one diafiltration step is performed between the chromatography steps, for example between the mixed-mode chromatography step and the cation exchange chromatography step, and one ultrafiltration/diafiltration step is performed after the chromatography steps. These filtration steps can be performed using commercially available filtration devices, e.g., available from GE Healthcare or Sartorius. The ultrafiltration is preferably performed using the Sartocon cassettes and Sartocon Slice cassettes supplied by Sartorius.

E. Produced Sialyltransferase Polypeptide

In another aspect, the present invention provides sialyltransferase polypeptides produced by any one of the methods according to the invention.

In one embodiment, the sialyltransferase polypeptide is a truncated sialyltransferase polypeptide lacking all or portion of the sialyltransferase signal domain, all or portion of the sialyltransferase transmembrane domain, and/or all or portion of the sialyltransferase stem domain. In a preferred embodiment of the present invention, the sialyltransferase polypeptide only comprises the sialyltransferase active domain, said polypeptide being soluble. In a most preferred embodiment, the sialyltransferase is ST6GalNAcI, preferably from chicken, most preferably the sialyltransferase is the protein according to SEQ ID NO:4 or SEQ ID NO: 6.

The sialyltransferase polypeptides produced according to the methods of the present invention have several advantages over sialyltransferase polypeptides from the prior art. The novel and improved production methods of the present invention provide sialyltransferase polypeptides which are highly active, purified to a pharmaceutical grade and amenable to large scale production.

The term "pure" refers to a sialyltransferase polypeptide that is substantially or essentially free from components which normally accompany the material in the mixture used to prepare the polypeptide, e.g. DNA or host cell proteins. Typically, the sialyltransferase polypeptide produced by the method of the present invention is at least 98% pure, preferably at least 99% pure. Purity is determined by any art-recognized method of analysis (e.g., band intensity on a silver stained gel, polyacrylamide gel electrophoresis, HPLC, RP-HPLC, ELISA, or a similar means).

The term "active" refers to the specific activity of a sialyltransferase polypeptide produced by the method of the present invention, that means the catalytic activity of the sialyltransferase, which is transferring a sialic acid moiety from a donor molecule to an acceptor molecule.

The catalytic activity of ST6GalNAcI refers to the transfer of a sialic acid moiety from CMP-sialic acid by an α2,6 linkage onto an N-acetylgalactosamine (GalNAc) residue O-linked to the amino acid threonine/serine of a glycoprotein. The specific activity may be expressed in activity units. As used herein, one activity unit catalyzes the formation of 1 µmol of product per minute at a given acceptor-substrate, temperature and pH value. In the present invention, the specific activity of ST6GalNAcI is in a range between 5 U/mg and 10 U/mg, preferably 6 U/mg to 9 U/mg, most preferably 7 U/mg to 8 U/mg.

The sialyltransferase activity may be determined by known methods. Such methods include fluorescence assay, RP-HPLC-based assays and radioactive approaches (Spiegel et al., 1992, *J Chromatogr.*, 573(1):23-7; Gross et al., 1990, *Anal Biochem.*, 186(1):127-34; Skretas et al., 2009, *Microbial cell factories*, 8:50).

F. Use of Sialyltransferases

In a further aspect, the present invention includes the use of the ST6GalNacI produced by the method according to the invention for the glycosylation of therapeutic proteins, in particular for the glyco-PEGylation of human G-CSF, erythropoietin, IFN, hGH, FSH, insulin or antibodies.

The glycosyltransferase ST6GalNAcI is an essential reagent for glycosylation of therapeutic proteins. Additionally, ST6GalNAcI is an important reagent for research and development of therapeutically important glycopeptides and oligosaccharide therapeutics.

The modified ST6GalNAcI sialyltransferase enzymes of the present invention are useful for in vivo and in vitro preparation of glycosylated peptides, as well as for the production of oligosaccharides containing the specific glycosyl residues that can be transferred by the modified glycosyltransferase enzymes of the present invention. Modified forms of ST6GalNAcI polypeptides can possess biological activities comparable to, and in some instances, in excess of their full-length polypeptide counterparts.

The term "glycosylation" as used herein, refers to the enzymatically mediated conjugation of a modified sugar species to an amino acid or glycosyl residue of a polypeptide, e.g., an erythropoietin peptide, by the sialyltransferase prepared by the method of the present invention. Subgenera of glycosylation are "glycoconjugation" and "glyco-PEGylation," in which the modifying group of the modified sugar is poly (ethylene glycol), an alkyl derivative (e.g., m-PEG) or reactive derivative (e.g., $H_2N$-PEG, HOOC-PEG) thereof.

A "therapeutic protein" as used herein, refers to a protein, peptide, glycoprotein or glycopeptide that is administered to a subject to treat a disease or dysfunction or to improve health of the subject. In a preferred embodiment the subject is a human. In a further preferred embodiment, the therapeutic protein is a human protein. In an additional embodiment, the therapeutic protein is glycosylated or otherwise modified by one or more glycosyltransferases produced in CHO cells.

G-CSF (Granulocyte-colony stimulating factor) is a hematopoietic growth factor that stimulates the proliferation and differentiation of hematopoietic precursor cells and the activation of mature neutrophils. G-CSF is capable of supporting neutrophil proliferation in vitro and in vivo. The human form of G-CSF was cloned by groups from Japan and the USA in 1986 (see e.g. Nagata et al., 1986, *Nature* 319: 415-418). The natural human glycoprotein exists in two forms, one having 174 and the other having 177 amino acids. The more abundant and more active 174 amino acid form has been used in the development of pharmaceutical products by recombinant DNA technology.

The following examples refer to the production and purification of a truncated chicken ST6GalNAcI polypeptide and are provided merely to further illustrate the method of the invention. The scope of the invention shall not be construed as merely consisting of the following examples.

EXAMPLES

1. Construction of the Expression Cassette

An expression cassette was generated for expression of an ST6GalNAcI polypeptide consisting of the chicken glycosyltransferase (α-N-acetyl-neuraminyl-2,3-β-galactosyl-1,3-N-Acetylgalactosaminide alpha-2,6-sialyltransferase I) N-terminally truncated at amino acid K232 to which 8 amino acids of an intervening sequence were attached to the N-terminus. The entire amino acid sequence used for expression is depicted in SEQ ID NO: 6.

To add a translation start signal and to increase the expression rate, the nucleic acid encoding the truncated ST6GalNAcI polypeptide was introduced into an expression cassette of genomic human erythropoietin (EPO) to replace the coding sequences of the EPO.

Overall the ST6GalNAcI transcription unit was designed to contain the following elements:

EPO signal sequence (consisting of the human erythropoietin exon 1 [coding for 4 amino acids], intron 1 and a portion of exon 2 [coding for 27 amino acids: MGVHECPAWLWLLLSLLSL PLGLPVLG]);

ST6GalNAcI and intervening sequence nucleotide sequence (SEQ ID NO: 5);

3'-UTR of human erythropoietin 285 bp;
45 bp linker with 5'-NotI site; the 3'-MunI site is an integral part of the SV40 sequence.

Based on the amino acid sequence as presented in SEQ ID NO: 6, the nucleotide sequence of the mature ST6GalNAcI was optimised for codon usage in CHO cells. However, the nucleotides derived from the genomic EPO sequence were not adapted and correspond to the natural human Erythropoietin sequence. The resulting expression cassette is abbreviated EcST6. The nucleotide sequence of EcST6 was confirmed by sequencing (SEQ ID NO: 7). Sequence congruence was 100%.

2. Construction of the Expression Vector

The synthetic EcST6 fragment was cloned as a NotI/MnuI fragment into the expression vector pMOZ-G8.

This vector is based on a pSV2 backbone which contains the β-lactamase expression unit which confers ampicillin resistance and the pBR322 origin of replication as prokaryotic elements and the eukaryotic selection marker dihydrofolate reductase (DHFR) driven by a SV40 early gene promoter and the corresponding SV40 3'-UTR. The original mouse DHFR selection marker was modified by partial fusion with a CHO DHFR gene to obtain a recombinant hybrid DHFR (DHFRec), which shows a 10-fold lower affinity to the selective agent methotrexate (MTX). Cells transfected with the DHFRec selection marker can be selected with higher amounts of MTX to block endogenous DHFR which is present in the progenitor CHOSI CHO DHFR-cell line first, and to enrich for genetically altered cells harbouring plasmid derived DHFRec only. Gene expression is under control of a strong mCMV promoter. Downstream of mCMV promoter is the multiple cloning site (MCS) and a rabbit β-globin intron as well as a 3'-UTR enabling the efficient expression of cDNA transcripts.

Insertion of the cassette into the vector pMOZ-G8 was verified by PCR.

*E. coli* cells were transformed with the expression plasmid pMO7-G8EcST6. Colony screening of different transformants was performed and plasmid DNA was prepared from a selected clone. To confirm the identity of pMO7-G8 EcST6, the entire nucleotide sequence was verified by DNA sequencing.

3. CHO Cell Line

For expression of the secreted form of the chicken ST6GalNAcI, a Chinese hamster ovary cell line was used. The parental cell line used for production of ST6GalNAcI is a derivative of a CHOSI 4, a Chinese hamster ovary cell line (CHO dhfr-) deficient in dihydrofolate reductase (dhfr) activity which has been adapted for growth in serum and protein free medium.

Summary of host cell line CHOSI 4:
The CHOSI 4 host cell line was derived from CHO dhfr- (ATCC number CRL-9096; ACC126 from DSMZ, Braunschweig, Germany).
The CHOSI 4 host cell line was adapted for growth in chemically defined, serum- and protein-free medium by long term cultivation in MAM-PF2 medium.
The morphology of CHOSI 4 is round in shape. The culture grows as a single cell suspension.
CHOSI 4 is adapted for growth in animal component free, chemical defined MAM-PF media, which do not contain serum, proteins, peptides or hydrolysates. Nevertheless, the cell line can be cultivated in other commercially available serum-free media.
CHOSI 4 is subcultured by a total split ratio of 1:50 per week. The cells are split first 1:20 into a new flask and after 4 days obtain 3/2 of the initial volume of fresh medium. CHOSI 4 shows a specific growth rate of more than one per day ($D>1\times d^{-1}$) and cell densities in stirred culture systems of $2\times10^6$ cells/mL in batch mode and $1\times10^7$ cells/mL in fed-batch mode.
Addition of attachment factors or foetal calf serum to the cell culture medium leads to a change of the cells morphology, and CHOSI 4 cells revert to an epithelial layer.

4. Cell Culture and Harvest

Thawing of Cells and Inoculum Expansion in T-Flasks and Spinner Flasks

A single vial of the MCB was taken out of storage in the vapour phase of liquid nitrogen and warmed in a water bath at $37\pm1°$ C. The cells were collected by centrifugation into a T-flask containing fresh, pre-warmed culture medium. Further inoculum expansion was achieved by dilution and subcultivation steps in spinner flasks with increasing volumes of culture medium to a final volume which is adequate for use as seed in the bioreactor.

Cell Expansion in the Seed Bioreactor

After cell expansion in spinner flasks the inoculum was transferred into the seed bioreactor and the volume was expanded with fresh medium to a final working volume of 10 L. Cells were cultured in the seed bioreactor for 3 days until the adequate cell number had been reached for inoculation of the production bioreactor.

Cultivation in the Production Bioreactor

Following growth in the seed bioreactor, the contents of the seed bioreactor was aseptically transferred into the production bioreactor and the transferred culture was expanded to the final working volume with fresh culture medium. After reaching a predefined cell density of $\geq1.5\times10^6$ viable cells/mL, the incubation temperature was lowered from $37°\pm1°$ C. to $32°\pm1°$ C. The glucose level was maintained within a defined range by feeding of a glucose solution at a concentration between 4 g/L and 8 g/L. The fermentation process was terminated 14-17 days after start of the cultivation in the production bioreactor.

Harvesting and Storage

The cell suspension of the production bioreactor was cleared from cells and debris by depth filtration of the harvest in sterile disposable bags after termination of the fermentation. A disposable depth filter was used for the filtration of the harvest. The harvest was stored at 2-8° C. until further downstream processing.

5. Purification

Purification

Example 1

The purification process of ST6GalNAcI started with a capture chromatography step using an anion exchange column. The subsequent purification steps included affinity chromatography, mixed-mode chromatography, ultra-/diafiltration, cation exchange chromatography and a final nanofiltration through a 15-nm Planova® membrane. The chromatographic steps were performed using gradient chromatography systems and ran automatically. UV adsorption, conductivity, pH, flow rate and back pressure were recorded at every chromatographic step by a suitable software.

The column types and resins used are presented in Table 1:

| Step | Column type | Resin type | Gel dimensions (D × H) [mm] |
|---|---|---|---|
| Anion Exchange Chromatography | Borosilicate glass column BPG | Q-Sepharose Fast Flow | 200 × 205 |
| Affinity Chromatography | Borosilicate glass column BPG | Blue Sepharose 6-Fast Flow | 140 × 110 |
| Mixed Mode Chromatography | Borosilicate glass column BPG | Hydroxyapatite Type I 40 μm | 100 × 250 |
| Cation Exchange Chromatography | Borosilicate glass column BPG | SP-Sepharose High performance | 100 × 150 |

1$^{st}$ Column: Anion Exchange Chromatography (Q-Sepharose FF)

Anion exchange chromatography with Q-Sepharose Fast Flow resin was used as the first chromatographic step to capture ST6GalNAcI in the harvest and for volume reduction. ST6GalNAcI was eluted by applying a salt step of 800 mM NaCl in 20 mM Tris HCl, pH 7.6. The eluate was collected based on the UV absorption profile.

Chromatographic conditions are summarized in Table 2:

| Parameter | Conditions |
|---|---|
| Resin | Q-Sepharose Fast Flow (Amersham Biociences/GE-Healthcare) |
| Column diameter | 200 mm |
| Bed height | 205 mm +/− 15 mm |
| Theoretical plates | >2,200 N/m |
| Asymmetry factor | 0.8-1.5 |
| Equilibration buffer | 20 mM Tris, pH 7.6 |
| Elution Buffer | 800 mM NaCl in 20 mM Tris HCl, pH 7.6 |
| Pooling criteria | Start: OD280 > 0.04 AU Stop: 0.6 CV after start |

2$^{nd}$ Column: Affinity Chromatography (Blue Sepharose 6 FF)

Blue Sepharose 6FF is an agarose resin covalently linked to the dye Cibacron Blue® and was used to preferentially bind ST6GalNAcI in the presence of contaminants contained in the Q-Sepharose eluate. ST6GalNAcI was eluted with 500 mM L-arginine hydrochloride in 25 mM potassium phosphate buffer, pH 7.5. The eluate was collected based on the UV absorption profile.

Chromatographic conditions are summarized in Table 3:

| Parameter | Conditions |
|---|---|
| Resin | Blue Sepharose FF (Amersham Biociences/GE-Healthcare) |
| Column diameter | 140 mm |
| Bed height | 110 mm +/− 20 mm |
| Theoretical plates | >2,778 N/m |
| Asymmetry factor | 0.8-1.5 |
| Equilibration buffer | 25 mM potassium phosphate buffer pH 7.5, 50 mM NaCl |
| Elution Buffer | 500 mM L-arginine hydrochloride 25 mM potassium phosphate pH 7.5 |
| Pooling criteria | Start: OD > 0.010 AU Stop: OD < 0.05 AU |

3$^{rd}$ Column: Mixed-Mode Chromatography (Hydroxyapatite)

Mixed-mode chromatography on a hydroxyapatite resin was used as an intermediate step to further reduce the levels of HCP and DNA. ST6GalNAcI was eluted with 1.0 M NaCl in 5 mM sodium phosphate buffer pH 6.8. The eluate was collected based on the UV absorption profile.

Chromatographic conditions are summarized in Table 4:

| Parameter | Conditions |
|---|---|
| Resin | Hydroxyapatite CHT Type I 40 μm (BioRad) |
| Column diameter | 100 mm |
| Bed height | 250 mm +/− 20 mm |
| Theoretical plates | >4,760 N/m |
| Asymmetry factor | 0.8-2.3 |
| Equilibration buffer | 5 mM Potassium phosphate buffer pH 6.8 |
| Elution Buffer | 5 mM Potassium phosphate buffer pH 6.8, 1M NaCl |
| Pooling criteria | Start: OD > 0.050 AU Stop: 1.34 CV |

Ultrafiltration/Diafiltration

The hydroxyapatite eluate was diafiltered using a Sartocon slice module with a molecular weight cut-off (MWCO) of 30 kDa. The tangential flow filtration was conducted to desalt and concentrate the product and finally exchange the buffer to 25 mM potassium phosphate buffer to pH 6.0.

4$^{th}$ Column: Cation Exchange Chromatography (SP Sepharose)

Cation exchange chromatography was used as the final polishing step to remove any possibly remaining residual HCP. Under the specific conditions applied ST6GalNAcI was eluted with 250 mM NaCl in 25 mM potassium phosphate buffer pH 6.0.

Chromatographic conditions are summarised in Table 5:

| Parameter | Conditions |
|---|---|
| Resin | SP-Sepharose High Performance |
| Column diameter | 100 mm |
| Bed height | 150 mm +/− 20 mm |
| Theoretical plates | >7,353 N/m |
| Asymmetry factor | 0.8-1.5 |
| Equilibration buffer | 25 mM potassium phosphate buffer pH 6.0 |
| Elution Buffer | 250 mM Sodium chloride, 25 mM Potassium phosphate pH 6.0 |
| Pooling criteria | Start OD > 0.050 AU Stop: OD < 0.200 AU + 0.6 CV |

Ultrafiltration/Diafiltration and Formulation

The SP-Sepharose eluate was diafiltrated in a Sartocon slice module with a MWCO of 30 kDa. The tangential flow filtration was conducted to desalt and concentrate the product and exchange the buffer to 50 mM BisTris, pH 6.5, 100 mM NaCl, 5% Sorbitol.

After completion of the diafiltration Tween 80 was added to a final concentration of 0.003%.

Purification

Example 2

1$^{st}$ Column: Anion Exchange Chromatography (Q Sepharose FF)

This process step is used for capture of cST6 by anion exchange chromatography from clarified, sterile filtered bioreactor harvest. 1000 mL supernatant from bioreactor was diluted 1:3 in Buffer A (20 mM Tris pH 7.6) and loaded on an omni 25/150 Q Sepharose FF column. The cST6 was eluted by a linear NaCl gradient (0-1 M, 20 CV).

2$^{Nd}$ Column: Affinity Chromatography (CDP Affinity Matrix)

This affinity chromatography process step is an intermediate step which is important to increase the cST6 purity. The pool of fractions 9-11 from the Q Sepharose capture step was diluted 1:3 in Buffer A (10 mM IVIES pH 6.8, 25% glycerol) and loaded on a XK 10/55 CDP Affinity column. To avoid overloading of the CDP column the load was applied in two identical CDP runs. The cST6 was eluted by a linear NaCl gradient (0-1 M, 10 CV).

3$^{Rd}$ Column: Anion Exchange Chromatography (Mono Q Sepharose)

This anion exchange chromatography was used as the final polishing step. The pool of the cST6 fractions from the CDP intermediate step was diluted 1:10 in Buffer A (20 mM Tris pH 7.6) and loaded on a Mono Q HR 10/10 column. The cST6 was eluted by a linear NaCl gradient (0-0.6 M, 5 CV).

Purification

Example 3

1$^{st}$ Column: Anion Exchange Chromatography (Q Sepharose FF)

Anion exchange chromatography with Q-Sepharose Fast Flow resin was used as the first chromatographic step to capture ST6GalNAcI in the harvest and for volume reduction. 300 mL clarified and sterile filtered supernatant from fed-batch cultivation bioreactor was purified.

Chromatographic conditions are summarized in Table 6:

| Column | Omnifit 25, bed height = 15 cm, CV = 73.6 mL |
|---|---|
| Equilibration buffer A | 20 mM Tris, pH 7.6 |
| Elution buffer B | 20 mM Tris, pH 7.6, 1M NaCl |
| Dilution factor for load | Sample dilution 1:3 in equilibration buffer A |
| Gradient | Steps: 4% (4CV), 20% (4 CV) and 100% (2 CV) elution buffer B |

2$^{nd}$ Column: Intermediate Affinity Chromatography (Blue Sepharose FF)

This affinity chromatography process step is an intermediate step which is important to increase the cST6 purity. Eluate of the capture chromatography step (29 mL) was diluted and purified by a Blue Sepharose chromatography step.

Chromatographic conditions are summarized in Table 7:

| Column | Omnifit 10, bed height = 7.0 cm, CV = 5.5 mL |
|---|---|
| Equilibration buffer A | 25 mM potassium phosphate, pH 7.5, 50 mM NaCl |
| Elution buffer B | 25 mM potassium phosphate, pH 7.5. 1M arginine-HCl |
| Dilution factor for load | Sample dilution 1:3 in equilibration buffer A |
| Gradient | Steps: 10% B, 75% B, 100% B, (each step 5CV) |

3$^{rd}$ Column: Polishing Affinity Chromatography (Prosep PB)

ProSep-PB media is composed of a synthetic m-aminophenyl ligand immobilized on controlled pore size glass beads.

This affinity chromatography was used as the final polishing step. 15 mL intermediate eluate was purified in this chromatography step.

Chromatographic conditions are summarized in Table 8:

| Column | Omnifit 10, bed height = 5.8 cm, CV = 4.55 mL |
|---|---|
| Equilibration buffer A12 | 25 mM potassiumphosphate, pH 6.5, 0.5M NaCl |
| Equilibration buffer A11 | 50 mM BisTris, pH 6.5, 0.5M NaCl |
| Elution buffer B | 50 mM BisTris, pH 6.5, 0.5M NaCl, 1.37M Sorbitol |
| Dilution factor for sample load | Dilution 1:5 in equilibration buffer A12 |
| Gradient | Step, 100% B over 5 CV |
| Dilution buffer | 50 mM BisTris, pH 6.5, 0.015% Tween80 |
| Formulation buffer | 50 mM BisTris, pH 6.5, 0.1M NaCl, 5% Sorbitol, 0.003% Tween80 |

6. ST6GalNAcI Purity, Specific Activity and Yield of Production

Example 1

The purity of the ST6GalNAcI purified according to example 1 was measured by Coomassie stained SDS-PAGE (see FIG. 3), RP-HPLC, ELISA, and Threshold assay in three batches. The specific activity of the ST6GalNAcI was measured by RP-HPLC.

Purity and specific activities were as shown in Table 9:

| Test | Method | Batch # 1 | Batch # 2 | Batch # 3 |
|---|---|---|---|---|
| Identity | SDS-PAGE | Main band at approx. 66 kDa. | Main band at approx. 66 kDa. | Main band at approx. 66 kDa. |
| Purity | RP-HPLC | 100.0% | 100.0% | 99.5% |
| Residual CHO host-cell protein (Generic assay) | ELISA | 35 ng/mg (ppm) | 35 ng/mg (ppm) | 37 ng/mg (ppm) |
| Residual host-cell DNA | Threshold assay | ≤784 pg/mg | ≤833 pg/mg | ≤755 pg/mg |
| Specific activity | RP-HPLC | 5.6 U/mg | 7.8 U/mg | 7.7 U/mg |

The yield of production of the purified ST6GalNacI was in a range from 65 mg/L to 75 mg/L.

A comparability study was made to compare the expression of ST6GalNAcI in CHO cells with the expression of ST6GalNAcI in insect cells. Insect cell-derived ST6GalNAcI showed a specific activity of 2.5 U/mg and the CHO-derived ST6GalNAcI showed a higher specific activity of 7.8 U/mg.

Example 2

Figure 4:
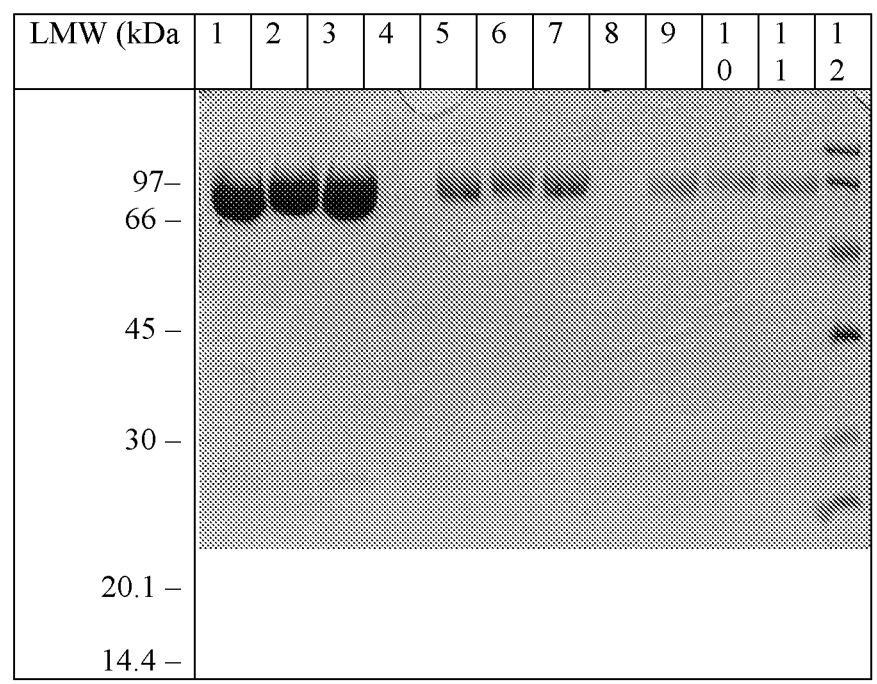

The purified cST6 fractions according to example 2 were pooled and analyzed for purity via Coomassie-stained SDS-PAGE (see FIG. 4). The cST6 sample pools coming from three different clones C1, C2 and C3 were loaded undiluted, diluted 1:5 and diluted 1:10.

Table 10 shows sample preparation and loading:

| Well | Sample | Sample volume [µl] | Sample buffer [µl] | Loading volume [µl] | Conditions |
|---|---|---|---|---|---|
| 1 | C1 pool after 3rd column (Mono Q) | 10 | 10 | 20 | boiling/reduced |
| 2 | C2 pool after 3rd column (Mono Q) | 10 | | | |
| 3 | C3 pool after 3rd column (Mono Q) | 10 | | | |
| 4 | — | — | 10 | 10 | |
| 5 | C1 pool after 3rd column (Mono Q) | 2 + 8 H2O | 10 | 20 | |
| 6 | C2 pool after 3rd column (Mono Q) | 2 + 8 H2O | | | |
| 7 | C3 pool after 3rd column (Mono Q) | 2 + 8 H2O | | | |
| 8 | — | | 10 | 10 | |
| 9 | C1 pool after 3rd column (Mono Q) | 1 + 9 H2O | 10 | 20 | |
| 10 | C2 pool after 3rd column (Mono Q) | 1 + 9 H2O | | | |
| 11 | C3 pool after 3rd column (Mono Q) | 1 + 9 H2O | | | |
| 12 | Low molecular weight marker | | | 10 | |

As shown in FIG. 4, the undiluted pools show minor contaminations below 20 kDa. The signal of the 1:10-diluted pools was stronger than the signal of the impurities in the undiluted samples. Thus the purity can be estimated to be >90%.

Example 3

The purity of the ST6GalNAcI purified according to example 3 was measured by Coomassie-stained SDS-PAGE, RP-HPLC, ELISA, and Threshold assay in three batches. The specific activity of the ST6GalNAcI was measured by RP-HPLC.

FIGURE LEGENDS

FIG. 1:
Sialyltransferase manufacturing process: cell culture and harvest

FIG. 2:
Sialyltransferase manufacturing process: purification

Figure 3:
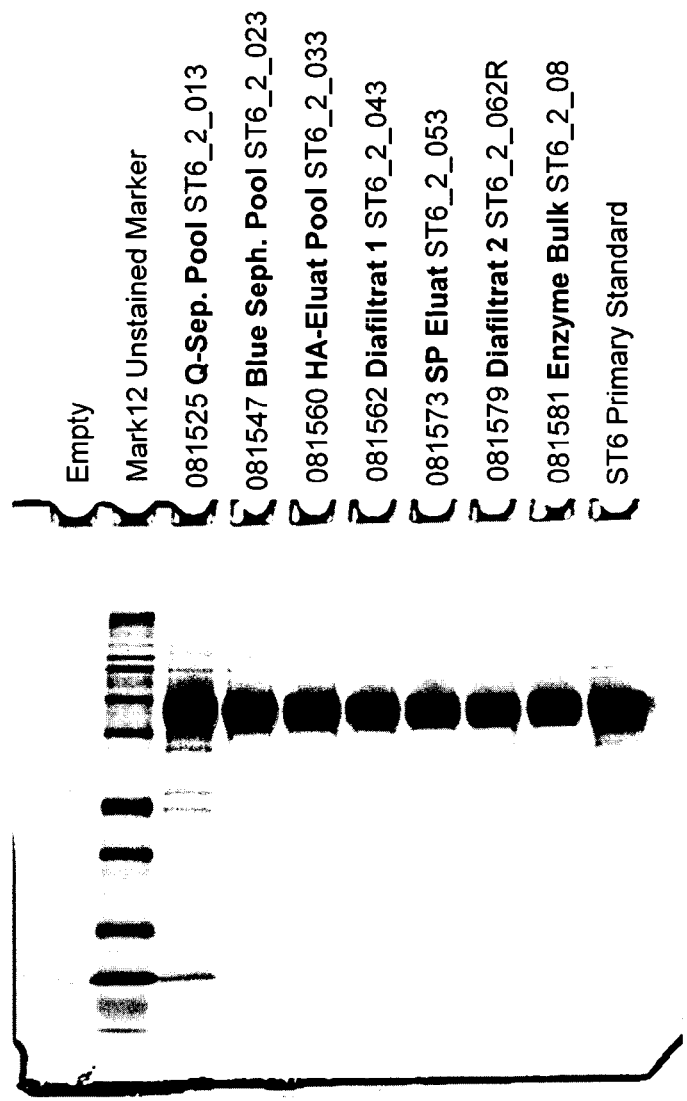

FIG. 3:
Protein gel (SDS-PAGE) that has been stained with Coomassie Blue after the different purification steps of example 1. The band at around 66 kDa corresponds to the purified ST6GalNAcI polypeptide according to SEQ ID NO: 6.

FIG. 4:
Protein gel (SDS-PAGE) stained with Coomassie Blue of cST6 pools from three different clones C1, C2 and C3 after third column of the purification according to example 2. The band at around 66 kDa corresponds to the purified ST6GalNAcI polypeptide according to SEQ ID NO:6.

The invention claimed is:

1. A method of producing a sialyltransferase polypeptide, which comprises the steps of:
   a) expressing a sialyltransferase polypeptide in Chinese hamster ovary cells; collecting the cell culture medium containing the expressed sialyltransferase polypeptide, wherein an expression cassette encoding an erythropoietin (EPO) signal sequence and a sialyltransferase polypeptide sequence is used for expressing the sialyltransferase polypeptide in Chinese hamster ovary cells;
   b) purifying the sialyltransferase polypeptide from the cell culture medium by subjecting the cell culture medium to (i) two affinity chromatography steps or one affinity chromatography step and one mixed-mode chromatography step, (ii) one anion exchange chromatography step and (iii) one cation exchange chromatography step; and
   c) obtaining an eluate comprising the purified sialyltransferase polypeptide.

2. The method according to claim 1, wherein the sialyltransferase is ST6GalNAcI.

3. The method according to claim 2, wherein the ST6GalNAcI is selected from the group consisting of: human, chimpanzee, orangutan, pig, cow, dog, rat, mouse and chicken ST6GalNAcI.

4. The method according to claim 2, wherein the ST6GalNAcI is a chicken ST6GalNAcI.

5. The method according to claim 2, wherein the ST6GalNAcI polypeptide comprises an amino acid sequence according to SEQ ID NO: 4 or SEQ ID NO: 6.

6. The method according to claim 1, wherein the sialyltransferase polypeptide consists of the sialyltransferase active domain.

7. The method according to claim 1, wherein the EPO signal sequence consists of the human erythropoietin exon 1, intron 1 and a portion of exon 2, wherein the portion of exon 2 codes for 27 amino acids comprising the following sequence: MGVHECPAWLWLLLSLLSLPLGLPVLG.

8. The method according to claim 1, wherein step a) is performed by applying an incubation temperature shift from 37° C.+/−1° C. to 32° C.+/−1° C. after reaching a cell density of equal or more than $5 \times 10^5$ viable cells/ml.

9. The method according to claim 1, wherein step b) is performed in the following order:
   i. an anion exchange chromatography;
   ii. a first affinity chromatography;
   iii. a second affinity chromatography or a mixed-mode chromatography;
   iv. a cation exchange chromatography.

10. The method according to claim 1, wherein the anion exchange chromatography is performed using a resin carrying a quaternary ammonium as a functional group.

11. The method according to claim 10, wherein the anion exchange chromatography is performed using a NaCl/Tris-HCl buffer as eluent at a pH in the range between 7.0 and 8.0.

12. The method according to claim 1, wherein the first affinity chromatography is performed using a dye affinity chromatography.

13. The method according to claim 12, wherein the first affinity chromatography is performed using a Blue Sepharose Fast Flow resin.

14. The method according to claim 13, wherein the Blue Sepharose affinity chromatography is performed using a L-arginine hydrochloride/potassium phosphate buffer as eluent at a pH in the range between 7.0 and 8.0.

15. The method according to claim 1, wherein the mixed-mode chromatography is performed using a hydroxyapatite resin.

16. The method according to claim 15, wherein the hydroxyapatite affinity chromatography is performed using a NaCl/potassium phosphate buffer as eluent at a pH in the range between 6.3 and 7.3.

17. The method according to claim 1, wherein the cation exchange chromatography is performed with a resin that contains sulfopropyl cation exchange material.

18. The method according to claim 17, wherein the cation exchange chromatography is performed using SP-Sepharose High Performance resin.

19. The method according to claim 18, wherein the cation exchange chromatography is performed using a NaCl/potassium phosphate buffer as eluent at a pH in the range between 6.0 and 7.0.

20. The method according to claim 1, wherein step b) is performed in the following order:
   i. an anion exchange chromatography using a Q-Sepharose Fast Flow resin;
   ii. an affinity chromatography using a Blue Sepharose Fast Flow resin;
   iii. a mixed-mode chromatography using a hydroxyapatite resin;
   iv. a cation exchange chromatography using a SP-Sepharose High Performance resin.

* * * * *

UNITED STATES PATENT AND TRADEMARK OFFICE
CERTIFICATE OF CORRECTION

PATENT NO. : 9,222,081 B2
APPLICATION NO. : 13/813804
DATED : December 29, 2015
INVENTOR(S) : Angermann et al.

It is certified that error appears in the above-identified patent and that said Letters Patent is hereby corrected as shown below:

On the title page, item (73),

The Assignee should read -

RATIOPHARM GMBH, ULM (DE)

Signed and Sealed this
Twenty-third Day of August, 2016

Michelle K. Lee
*Director of the United States Patent and Trademark Office*

SEQUENCE LISTING

<160> NUMBER OF SEQ ID NOS: 7

<210> SEQ ID NO 1
<211> LENGTH: 1701
<212> TYPE: DNA
<213> ORGANISM: Gallus gallus

<400> SEQUENCE: 1

```
atggggtttt taatcagaag gcttcctaaa gattccagaa tattccgttg gctccttatt      60
ttaacagtct tttccttcat cattactagt tttagcgcct tgtttggcat ggagaaaagc     120
attttcaggc agctcaagat ttaccaaagc attgcacata tgctacaagt ggacacccaa     180
gatcagcaag gttcaaacta ttctgctaat gggagaattt caaaggttgg tttggagaga     240
gacattgcat ggctcgaact gaatactgct gtgagtacac caagtgggga agggaaggaa     300
gagcagaaga aaacagtgaa accagttgcc aaggtggaag aagccaagga gaaagtgact     360
gtgaaaccat tccctgaggt gatggggatc acaaatacaa cagcatcaac agcctctgtg     420
gtggagagaa caaaggagaa aacaacagcg agaccagttc caggggtggg ggaagctgat     480
gggaagagaa caacgatagc acttcccagc atgaaggaag acaaagagaa ggcgactgtg     540
aaaccatcct ttgggatgaa ggtagctcat gcaaacagca catccaaaga taaaccaaag     600
```

```
gcagaagagc ctcctgcatc agtgaaagcc ataagacctg tgactcaggc tgccacagtg      660
acagagaaga agaaactgag ggctgctgac ttcaagactg agccacagtg ggattttgat      720
gatgagtaca tactggatag ctcatctcca gtatcgacct gctctgaatc agtgagagcc      780
aaggctgcca agtctgactg gctgcgagat cttttcctgc cgaacatcac actcttcata      840
gacaagagtt acttcaatgt cagtgagtgg gaccgcctgg agcattttgc acctccctat      900
ggcttcatgg agctgaatta ctcactggta gaagaagtca tgtcacggct gcctccaaat      960
ccccaccagc agctgctcct ggccaacagt agcagcaacg tgtcaacgtg catcagctgt      1020
gctgttgtgg ggaatggagg gatattgaat aactctggaa tgggccagga gattgactcc      1080
catgactatg tgttccgggt gagcggggct gtaatcaaag gttacgaaaa ggatgtggga      1140
acaaaaacct ccttctacgg attcacagcg tactccctgg tgtcctctct ccagaacttg      1200
ggacacaaag ggttcaagaa gatcccacag gggaagcata tcagatacat tcacttcctg      1260
gaggcagtta gagactatga gtggctgaag gctcttctgt tggacaagga tatcaggaaa      1320
ggattcctga actactatgg gcgaaggccc cgggagagat tcgatgaaga tttcacaatg      1380
aataagtacc tggtagctca ccctgatttc ctcagatact tgaaaaacag gttcttaaaa      1440
tctaaaaatc tgcaaaagcc ctactggcgg ctgtacagac ccacaacagg agccctcctg      1500
ctgctgactg ccctgcatct ctgtgaccgg gtgagtgcct atggctacat cacagaaggt      1560
caccagaagt actcggatca ctactatgac aaggagtgga aacgcctggt cttctacgtt      1620
aaccatgact tcaacttgga gaagcaggtg tggaaaaggc ttcatgatga aacatcatg      1680 aagctctacc agagatcctg a                                                1701
```

<210> SEQ ID NO 2
<211> LENGTH: 566
<212> TYPE: PRT
<213> ORGANISM: Gallus gallus

<400> SEQUENCE: 2

```
Met Gly Phe Leu Ile Arg Arg Leu Pro Lys Asp Ser Arg Ile Phe Arg
1               5                   10                  15

Trp Leu Leu Ile Leu Thr Val Phe Ser Phe Ile Ile Thr Ser Phe Ser
            20                  25                  30

Ala Leu Phe Gly Met Glu Lys Ser Ile Phe Arg Gln Leu Lys Ile Tyr
        35                  40                  45

Gln Ser Ile Ala His Met Leu Gln Val Asp Thr Gln Asp Gln Gln Gly
    50                  55                  60

Ser Asn Tyr Ser Ala Asn Gly Arg Ile Ser Lys Val Gly Leu Glu Arg
65                  70                  75                  80

Asp Ile Ala Trp Leu Glu Leu Asn Thr Ala Val Ser Thr Pro Ser Gly
                85                  90                  95

Glu Gly Lys Glu Glu Gln Lys Lys Thr Val Lys Pro Val Ala Lys Val
            100                 105                 110

Glu Glu Ala Lys Glu Lys Val Thr Val Lys Pro Phe Pro Glu Val Met
        115                 120                 125

Gly Ile Thr Asn Thr Thr Ala Ser Thr Ala Ser Val Val Glu Arg Thr
    130                 135                 140

Lys Glu Lys Thr Thr Ala Arg Pro Val Pro Gly Val Gly Glu Ala Asp
145                 150                 155                 160

Gly Lys Arg Thr Thr Ile Ala Leu Pro Ser Met Lys Glu Asp Lys Glu
                165                 170                 175
```

-continued

```
Lys Ala Thr Val Lys Pro Ser Phe Gly Met Lys Val Ala His Ala Asn
            180                 185                 190
Ser Thr Ser Lys Asp Lys Pro Lys Ala Glu Glu Pro Pro Ala Ser Val
        195                 200                 205
Lys Ala Ile Arg Pro Val Thr Gln Ala Ala Thr Val Thr Glu Lys Lys
    210                 215                 220
Lys Leu Arg Ala Ala Asp Phe Lys Thr Glu Pro Gln Trp Asp Phe Asp
225                 230                 235                 240
Asp Glu Tyr Ile Leu Asp Ser Ser Pro Val Ser Thr Cys Ser Glu
                245                 250                 255
Ser Val Arg Ala Lys Ala Lys Ser Asp Trp Leu Arg Asp Leu Phe
        260                 265                 270
Leu Pro Asn Ile Thr Leu Phe Ile Asp Lys Ser Tyr Phe Asn Val Ser
    275                 280                 285
Glu Trp Asp Arg Leu Glu His Phe Ala Pro Pro Tyr Gly Phe Met Glu
        290                 295                 300
Leu Asn Tyr Ser Leu Val Glu Glu Val Met Ser Arg Leu Pro Pro Asn
305                 310                 315                 320
Pro His Gln Gln Leu Leu Leu Ala Asn Ser Ser Asn Val Ser Thr
                325                 330                 335
Cys Ile Ser Cys Ala Val Val Gly Asn Gly Gly Ile Leu Asn Asn Ser
            340                 345                 350
Gly Met Gly Gln Glu Ile Asp Ser His Asp Tyr Val Phe Arg Val Ser
        355                 360                 365
Gly Ala Val Ile Lys Gly Tyr Glu Lys Asp Val Gly Thr Lys Thr Ser
    370                 375                 380
Phe Tyr Gly Phe Thr Ala Tyr Ser Leu Val Ser Ser Leu Gln Asn Leu
385                 390                 395                 400
Gly His Lys Gly Phe Lys Lys Ile Pro Gln Gly Lys His Ile Arg Tyr
                405                 410                 415
Ile His Phe Leu Glu Ala Val Arg Asp Tyr Glu Trp Leu Lys Ala Leu
            420                 425                 430
Leu Leu Asp Lys Asp Ile Arg Lys Gly Phe Leu Asn Tyr Tyr Gly Arg
        435                 440                 445
Arg Pro Arg Glu Arg Phe Asp Glu Asp Phe Thr Met Asn Lys Tyr Leu
    450                 455                 460
Val Ala His Pro Asp Phe Leu Arg Tyr Leu Lys Asn Arg Phe Leu Lys
465                 470                 475                 480
Ser Lys Asn Leu Gln Lys Pro Tyr Trp Arg Leu Tyr Arg Pro Thr Thr
                485                 490                 495
Gly Ala Leu Leu Leu Leu Thr Ala Leu His Leu Cys Asp Arg Val Ser
            500                 505                 510
Ala Tyr Gly Tyr Ile Thr Glu Gly His Gln Lys Tyr Ser Asp His Tyr
        515                 520                 525
Tyr Asp Lys Glu Trp Lys Arg Leu Val Phe Tyr Val Asn His Asp Phe
    530                 535                 540
Asn Leu Glu Lys Gln Val Trp Lys Arg Leu His Asp Glu Asn Ile Met
545                 550                 555                 560
Lys Leu Tyr Gln Arg Ser
                565
```

<210> SEQ ID NO 3
<211> LENGTH: 1008
<212> TYPE: DNA
<213> ORGANISM: Gallus gallus

<400> SEQUENCE: 3

```
aaaaccgagc ctcaatggga ttttgatgat gagtacatcc tggattccag ctccccagct      60
agcacctgtt ccgaaagcgt gagagccaag gctgccaaat ctgattggct cgcgacctg     120
tttctgccta atatcaccct gttcatcgac aagtcttact tcaatgtgtc tgagtgggac     180
aggctggaac attttgctcc accttatgga ttcatggagc tcaactacag cctggtggag     240
gaggtgatga gcaggctccc tcccaacccc caccagcagc tgctgctggc taattcttct     300
tctaacgtga gcacatgcat ctcctgtgca gtggtgggca atgggggat tctgaacaat     360
agcggtatgg gtcaggagat cgactctcat gattacgtgt tcagggtgtc tggcgctgtg     420
atcaaaggct atgagaagga cgtggggaca aaaacttcct tctacggctt cactgcctat     480
agcctcgtca gctccttgca aaacctcggg cataaggggt taagaaaaat cccacagggg     540
aagcatatca ggtacattca cttcctcgag gcagtgaggg actatgagtg gctgaaagcc     600
ctgctgttgg ataaggacat caggaaggga ttcctgaact attacggtcg caggcccagg     660
gagaggttcg acgaggactt caccatgaac aaatacctgg tcgctcaccc cgactttctg     720
aggtacctga gaataggtt cttgaaatct aaaaacctgc agaaacccta ttggaggctg     780
tacaggccta ccaccggggc tctgctcctg ctgactgctc tgcatctgtg cgacagggta     840
tctgcttacg gatacatcac cgagggccac caaaagtaca gcgaccatta ttatgacaaa     900
gaatggaagc ggctggtgtt ttacgtgaac cacgatttta atctggagaa gcaggtgtgg     960
aaaaggctcc acgacgagaa tatcatgaag ctgtatcaac ggagctga              1008
```

<210> SEQ ID NO 4
<211> LENGTH: 335
<212> TYPE: PRT
<213> ORGANISM: Gallus gallus

<400> SEQUENCE: 4

```
Lys Thr Glu Pro Gln Trp Asp Phe Asp Asp Glu Tyr Ile Leu Asp Ser
1               5                   10                  15

Ser Ser Pro Ala Ser Thr Cys Ser Glu Ser Val Arg Ala Lys Ala Ala
            20                  25                  30

Lys Ser Asp Trp Leu Arg Asp Leu Phe Leu Pro Asn Ile Thr Leu Phe
        35                  40                  45

Ile Asp Lys Ser Tyr Phe Asn Val Ser Glu Trp Asp Arg Leu Glu His
    50                  55                  60

Phe Ala Pro Pro Tyr Gly Phe Met Glu Leu Asn Tyr Ser Leu Val Glu
65                  70                  75                  80

Glu Val Met Ser Arg Leu Pro Pro Asn Pro His Gln Gln Leu Leu Leu
                85                  90                  95

Ala Asn Ser Ser Ser Asn Val Ser Thr Cys Ile Ser Cys Ala Val Val
            100                 105                 110

Gly Asn Gly Gly Ile Leu Asn Asn Ser Gly Met Gly Gln Glu Ile Asp
        115                 120                 125

Ser His Asp Tyr Val Phe Arg Val Ser Gly Ala Val Ile Lys Gly Tyr
    130                 135                 140

Glu Lys Asp Val Gly Thr Lys Thr Ser Phe Tyr Gly Phe Thr Ala Tyr
145                 150                 155                 160
```

```
Ser Leu Val Ser Ser Leu Gln Asn Leu Gly His Lys Gly Phe Lys Lys
            165                 170                 175

Ile Pro Gln Gly Lys His Ile Arg Tyr Ile His Phe Leu Glu Ala Val
        180                 185                 190

Arg Asp Tyr Glu Trp Leu Lys Ala Leu Leu Leu Asp Lys Asp Ile Arg
    195                 200                 205

Lys Gly Phe Leu Asn Tyr Tyr Gly Arg Arg Pro Arg Glu Arg Phe Asp
210                 215                 220

Glu Asp Phe Thr Met Asn Lys Tyr Leu Val Ala His Pro Asp Phe Leu
225                 230                 235                 240

Arg Tyr Leu Lys Asn Arg Phe Leu Lys Ser Lys Asn Leu Gln Lys Pro
                245                 250                 255

Tyr Trp Arg Leu Tyr Arg Pro Thr Thr Gly Ala Leu Leu Leu Leu Thr
            260                 265                 270

Ala Leu His Leu Cys Asp Arg Val Ser Ala Tyr Gly Tyr Ile Thr Glu
        275                 280                 285

Gly His Gln Lys Tyr Ser Asp His Tyr Tyr Asp Lys Glu Trp Lys Arg
    290                 295                 300

Leu Val Phe Tyr Val Asn His Asp Phe Asn Leu Glu Lys Gln Val Trp
305                 310                 315                 320

Lys Arg Leu His Asp Glu Asn Ile Met Lys Leu Tyr Gln Arg Ser
                325                 330                 335

<210> SEQ ID NO 5
<211> LENGTH: 1032
<212> TYPE: DNA
<213> ORGANISM: Artificial Sequence
<220> FEATURE:
<223> OTHER INFORMATION: truncated  chicken ST6GalNacI with intervening
      sequence

<400> SEQUENCE: 5
tttgtgtcta cccctggagga cccaaaaacc gagcctcaat gggatttga tgatgagtac      60 atcctggatt ccagctcccc agctagcacc tgttccgaaa gcgtgagagc caaggctgcc    120
aaatctgatt ggctgcgcga cctgtttctg cctaatatca ccctgttcat cgacaagtct    180
tacttcaatg tgtctgagtg ggacaggctg gaacattttg ctccacctta tggattcatg    240
gagctcaact acagcctggt ggaggaggtg atgagcaggc tccctcccaa cccccaccag    300
cagctgctgc tggctaattc ttcttctaac gtgagcacat gcatctcctg tgcagtggtg    360
ggcaatgggg ggattctgaa caatagcggt atgggtcagg agatcgactc tcatgattac    420
gtgttcaggg tgtctggcgc tgtgatcaaa ggctatgaga aggacgtggg gacaaaaact    480
tccttctacg gcttcactgc ctatagcctc gtcagctcct tgcaaaacct cgggcataag    540
gggtttaaga aaatcccaca ggggaagcat atcaggtaca ttcacttcct cgaggcagtg    600
agggactatg agtggctgaa agccctgctg ttggataagg acatcaggaa gggattcctg    660
aactattacg gtcgcaggcc cagggagagg ttcgacgagg acttcaccat gaacaaatac    720
ctggtcgctc accccgactt tctgaggtac ctgaagaata ggttcttgaa atctaaaaac    780
ctgcagaaac cctattggag gctgtacagg cctaccaccg gggctctgct cctgctgact    840
gctctgcatc tgtgcgacag ggtatctgct tacggataca tcaccgaggg ccaccaaaag    900
tacagcgacc attattatga caaagaatgg aagcggctgg tgttttacgt gaaccacgat    960
tttaatctgg agaagcaggt gtggaaaagg ctccacgacg agaatatcat gaagctgtat   1020
caacggagct ga                                                        1032
```

<210> SEQ ID NO 6
<211> LENGTH: 343
<212> TYPE: PRT
<213> ORGANISM: Artificial Sequence
<220> FEATURE:
<223> OTHER INFORMATION: truncated chicken ST6GalNacI with intervening sequence

<400> SEQUENCE: 6

```
Phe Val Ser Thr Leu Glu Asp Pro Lys Thr Glu Pro Gln Trp Asp Phe
1               5                   10                  15

Asp Asp Glu Tyr Ile Leu Asp Ser Ser Pro Ala Ser Thr Cys Ser
            20                  25                  30

Glu Ser Val Arg Ala Lys Ala Ala Lys Ser Asp Trp Leu Arg Asp Leu
            35                  40                  45

Phe Leu Pro Asn Ile Thr Leu Phe Ile Asp Lys Ser Tyr Phe Asn Val
        50                  55                  60

Ser Glu Trp Asp Arg Leu Glu His Phe Ala Pro Pro Tyr Gly Phe Met
65                  70                  75                  80

Glu Leu Asn Tyr Ser Leu Val Glu Val Met Ser Arg Leu Pro Pro
                85                  90                  95

Asn Pro His Gln Gln Leu Leu Ala Asn Ser Ser Ser Asn Val Ser
            100                 105                 110

Thr Cys Ile Ser Cys Ala Val Val Gly Asn Gly Gly Ile Leu Asn Asn
            115                 120                 125

Ser Gly Met Gly Gln Glu Ile Asp Ser His Asp Tyr Val Phe Arg Val
        130                 135                 140

Ser Gly Ala Val Ile Lys Gly Tyr Glu Lys Asp Val Gly Thr Lys Thr
145                 150                 155                 160

Ser Phe Tyr Gly Phe Thr Ala Tyr Ser Leu Val Ser Ser Leu Gln Asn
                165                 170                 175

Leu Gly His Lys Gly Phe Lys Lys Ile Pro Gln Gly Lys His Ile Arg
            180                 185                 190

Tyr Ile His Phe Leu Glu Ala Val Arg Asp Tyr Glu Trp Leu Lys Ala
        195                 200                 205

Leu Leu Leu Asp Lys Asp Ile Arg Lys Gly Phe Leu Asn Tyr Tyr Gly
    210                 215                 220

Arg Arg Pro Arg Glu Arg Phe Asp Glu Asp Phe Thr Met Asn Lys Tyr
225                 230                 235                 240

Leu Val Ala His Pro Asp Phe Leu Arg Tyr Leu Lys Asn Arg Phe Leu
                245                 250                 255

Lys Ser Lys Asn Leu Gln Lys Pro Tyr Trp Arg Leu Tyr Arg Pro Thr
            260                 265                 270

Thr Gly Ala Leu Leu Leu Leu Thr Ala Leu His Leu Cys Asp Arg Val
        275                 280                 285

Ser Ala Tyr Gly Tyr Ile Thr Glu Gly His Lys Tyr Ser Asp His
    290                 295                 300

Tyr Tyr Asp Lys Glu Trp Lys Arg Leu Val Phe Tyr Val Asn His Asp
305                 310                 315                 320

Phe Asn Leu Glu Lys Gln Val Trp Lys Arg Leu His Asp Glu Asn Ile
                325                 330                 335

Met Lys Leu Tyr Gln Arg Ser
            340
```

<210> SEQ ID NO 7
<211> LENGTH: 2235
<212> TYPE: DNA
<213> ORGANISM: Artificial Sequence
<220> FEATURE:
<223> OTHER INFORMATION: expression cassette EcST6

<400> SEQUENCE: 7

```
gcggccgctc tagaactagt ggatccccg ggctgcagga attcgatcgc gccccaggtc      60
gctgagggac cccggccagg cgcggagatg ggggtgcacg gtgagtactc gcgggctggg     120
cgctcccgcc cgcccgggtc cctgtttgag cggggattta gcgccccggc tattggccag     180
gaggtggctg ggttcaagga ccggcgactt gtcaaggacc ccggaagggg gaggggggtg     240
gggcagcctc cacgtgccag cggggacttg ggggagtcct tggggatggc aaaaacctga     300
cctgtgaagg ggacacagtt tgggggttga ggggaagaag gtttgggggt tctgctgtgc     360
cagtggagag gaagctgata agctgataac ctgggcgctg gagccaccac ttatctgcca     420
gaggggaagc ctctgtcaca ccaggattga agtttggccg gagaagtgga tgctggtagc     480
tgggggtggg gtgtgcacac ggcagcagga ttgaatgaag gccagggagg cagcacctga     540
gtgcttgcat ggttggggac aggaaggacg agctggggca gagacgtggg gatgaaggaa     600
gctgtccttc cacagccacc cttctccctc cccgcctgac tctcagcctg ctatctgtt      660
ctagaatgtc ctgcctggct gtggcttctc ctgtccctgc tgtcgctccc tctgggcctc     720
ccagtcctgg gctttgtgtc taccctggag gacccaaaaa ccgagcctca atgggatttt     780
gatgatgagt acatcctgga ttccagctcc ccagctagca cctgttccga aagcgtgaga     840
gccaaggctg ccaaatctga ttggctgcgc gacctgtttc tgcctaatat caccctgttc     900
atcgacaagt cttacttcaa tgtgtctgag tgggacaggc tggaacattt tgctccacct     960
tatggattca tggagctcaa ctacagcctg gtggaggagg tgatgagcag gctccctccc    1020
aaccccacc agcagctgct gctggctaat tcttcttcta acgtgagcac atgcatctcc    1080
tgtgcagtgg tgggcaatgg ggggattctg aacaatagcg gtatgggtca ggagatcgac    1140
tctcatgatt acgtgttcag ggtgtctggc gctgtgatca aaggctatga agaggacgtg    1200
gggacaaaaa cttccttcta cggcttcact gcctatagcc tcgtcagctc cttgcaaaac    1260
ctcgggcata aggggtttaa gaaaatccca caggggaagc atatcaggta cattcacttc    1320
ctcgaggcag tgagggacta tgagtggctg aaagccctgc tgttggataa ggacatcagg    1380
aagggattcc tgaactatta cggtcgcagg cccagggaga ggttcgacga ggacttcacc    1440
atgaacaaat acctggtcgc tcaccccgac tttctgaggt acctgaagaa taggttcttg    1500
aaatctaaaa acctgcagaa accctattgg aggctgtaca ggcctaccac cggggctctg    1560
ctcctgctga ctgctctgca tctgtgcgac agggtatctg cttacggata catcaccgag    1620
ggccaccaaa agtacagcga ccattattat gacaaagaat ggaagcggct ggtgttttac    1680
gtgaaccacg attttaatct ggagaagcag gtgtggaaaa ggctccacga cgagaatatc    1740
atgaagctgt atcaacggag ctgaccaggt gtgtccacct gggcatatcc accacctccc    1800
tcaccaacat tgcttgtgcc acaccctccc ccgccactcc tgaacccgt cgaggggctc    1860
tcagctcagc gccagcctgt cccatggaca ctccagtgcc agcaatgaca tctcagggc    1920
cagaggaact gtccagagag caactctgag atctttttcc ctctgccaaa aattatgggg    1980
acatcatgaa gccccttgag catctgactt ctggctaata aaggaaattt attttcattg    2040
caatagtgtg ttggaatttt ttgtgtctct cactcggaag gacatagatc cagacatgat    2100
```

-continued

```
aagatacatt gatgagtttg gacaaaccac aactagaatg cagtgaaaaa aatgctttat    2160
ttgtgaaatt tgtgatgcta ttgctttatt tgtaaccatt ataagctgca ataaacaagt    2220
taacaacaac aattg                                                     2235
```